US012721909B2

(12) United States Patent
Leavitt et al.

(10) Patent No.: US 12,721,909 B2
(45) **Date of Patent: *Sep. 1, 2026**

(54) COMPOSITIONS AND SYSTEMS COMPRISING TRANSFECTION-COMPETENT VESICLES FREE OF ORGANIC-SOLVENTS AND DETERGENTS AND METHODS RELATED THERETO

(71) Applicant: The University of British Columbia, Vancouver (CA)

(72) Inventors: Blair Leavitt, Vancouver (CA); Pieter Cullis, Vancouver (CA); Terri Petkau, Vancouver (CA); Austin Hill, Vancouver (CA); Pamela Wagner, Vancouver (CA); Jayesh Kulkarni, Vancouver (CA)

(73) Assignee: The University of British Columbia, Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 18/660,467

(22) Filed: May 10, 2024

(65) Prior Publication Data

US 2024/0350676 A1 Oct. 24, 2024

Related U.S. Application Data

(62) Division of application No. 17/281,678, filed as application No. PCT/US2019/055472 on Oct. 9, 2019, now Pat. No. 11,980,673.

(Continued)

(51) Int. Cl.

*A61K 48/00* (2006.01)
*A61K 9/1272* (2025.01)

(Continued)

(52) U.S. Cl.

CPC ........ *A61K 48/0091* (2013.01); *A61K 9/1272* (2013.01); *A61K 9/1277* (2013.01);

(Continued)

(58) Field of Classification Search

None

See application file for complete search history.

(56) References Cited

U.S. PATENT DOCUMENTS 5,552,155 A 9/1996 Bailey et al.
5,776,486 A 7/1998 Castor et al.

(Continued)

FOREIGN PATENT DOCUMENTS

WO 2007/051303 5/2007
WO 2008/040556 4/2008

(Continued)

OTHER PUBLICATIONS

Ammar Ehab et al. "Alzheimer's disease and its current treatments; Is there a possibility for a cure?" Open Journal of Chemistry, 5(1), 2019, DOI: http://dx.doi.org/10.17352/ojc.000012, pp. 013-019. (Year: 2019).*

(Continued)

*Primary Examiner* — Isaac Shomer

(74) *Attorney, Agent, or Firm* — Robin L. Teskin; Baker, Donelson, Bearman, Caldwell & Berkowitz PC

(57) ABSTRACT

Lipid-based vesicles, typically herein called transfection competent vesicles (TCVs), configured to safely and efficiently deliver DNA, RNA, other nucleic acid and protein cargoes into target cells. The safety and efficiency are each, and both, achieved in part by eliminating organic solvents such as ethanol and detergents such as sodium dodecyl sulfate from the TCV loading processes (i.e., inserting a cargo into the TCV), TCV storage processes, and/or TCV delivery processes. The cargoes can also comprise nucleic (Continued)

acids complexed with a protein, such as a ribonucleoprotein (RNP). The systems, compositions, devices and methods, etc., herein, in some embodiments, can provide empty TCVs that can if desired be loaded at the bench without use of specialized equipment.

7 Claims, 14 Drawing Sheets

Related U.S. Application Data

(60) Provisional application No. 62/743,116, filed on Oct. 9, 2018.

(51) Int. Cl.
*A61K 9/1277* (2025.01)
*A61K 31/7105* (2006.01)
*A61K 38/46* (2006.01)
*A61K 47/10* (2017.01)
*A61K 47/18* (2017.01)
*A61K 47/24* (2006.01)
*A61K 47/28* (2006.01)

(52) U.S. Cl.
CPC ........ *A61K 31/7105* (2013.01); *A61K 38/465* (2013.01); *A61K 47/10* (2013.01); *A61K 47/18* (2013.01); *A61K 47/186* (2013.01); *A61K 47/24* (2013.01); *A61K 47/28* (2013.01)

(56) References Cited

U.S. PATENT DOCUMENTS 6,093,816 A 7/2000 Lin et al.
6,096,720 A 8/2000 Love et al.
6,110,745 A 8/2000 Zhang et al.
6,693,086 B1 2/2004 Dow et al.
6,815,432 B2 11/2004 Wheeler et al.
7,060,689 B2 6/2006 Goins et al.
7,262,173 B2 8/2007 Kasid et al.
7,364,750 B2 4/2008 Finn et al.
7,678,415 B2 3/2010 Kato et al.
7,713,942 B2 5/2010 Dalsgaard et al.
7,741,300 B2 6/2010 Dow et al.
7,807,815 B2 10/2010 MacLachlan et al.
7,829,113 B2 11/2010 Okada et al.
7,838,658 B2 11/2010 MacLachlan et al.
7,901,708 B2 3/2011 MacLachlan et al.
7,982,027 B2 7/2011 MacLachlan et al.
8,021,686 B2 9/2011 Semple et al.
8,058,069 B2 11/2011 Yaworski et al.
8,101,741 B2 1/2012 MacLachlan et al.
8,158,601 B2 4/2012 Chen et al.
8,268,796 B2 9/2012 Ryan
8,283,333 B2 10/2012 Yaworski et al.
8,466,122 B2 6/2013 Heyes et al.
8,569,256 B2 10/2013 Heyes et al.
8,664,194 B2 3/2014 de Fougerolles et al.
8,741,866 B2 6/2014 Sah et al.
8,802,644 B2 8/2014 Chen et al.
8,883,202 B2 11/2014 Manoharan et al.
8,895,717 B2 11/2014 Sood et al.
8,906,873 B2 12/2014 Hung et al.
8,936,942 B2 1/2015 Heyes et al.
8,956,572 B2 2/2015 Knopov et al.
8,999,950 B2 4/2015 MacLachlan et al.
9,006,191 B2 4/2015 MacLachlan et al.
9,006,417 B2 4/2015 Yaworski et al.
9,012,498 B2 4/2015 Manoharan et al.
9,126,966 B2 9/2015 Martin et al.
9,254,265 B2 2/2016 Geall et al.
9,308,281 B2 4/2016 Guild et al.
9,326,940 B2 5/2016 Lee et al.
9,404,127 B2 8/2016 Yaworski et al.
9,439,858 B2 9/2016 Kim et al.
9,453,060 B2 9/2016 Montclare et al.
9,522,176 B2 12/2016 DeRosa et al.
9,579,338 B2 2/2017 Knopov et al.
9,616,032 B2 4/2017 Emanuel et al.
9,629,804 B2 4/2017 Heartlein et al.
9,758,795 B2 9/2017 Cullis et al.
9,814,760 B2 11/2017 Bancel et al.
9,868,691 B2 1/2018 Benenato
9,926,560 B2 3/2018 MacLachlan et al.
10,022,455 B2 7/2018 Derosa et al.
10,047,355 B2 8/2018 Yin et al.
10,064,935 B2 9/2018 Ciaramella et al.
10,077,232 B2 9/2018 Heyes et al.
10,087,247 B2 10/2018 Heartlein et al.
10,130,649 B2 11/2018 Derosa et al.
10,143,758 B2 12/2018 Guild et al.
10,172,924 B2 1/2019 DeRosa et al.
10,195,156 B2 2/2019 Benenato et al.
10,207,010 B2 2/2019 Besin et al.
10,245,229 B2 4/2019 Heartlein et al.
10,253,312 B2 4/2019 Maeder et al.
10,266,559 B2 4/2019 DeRosa et al.
10,292,932 B2 5/2019 Kim et al.
10,441,659 B2 10/2019 Payne et al.
10,501,513 B2 12/2019 De Fougerolles et al.
10,555,910 B2 2/2020 Lee
10,561,610 B2 2/2020 De Beer
10,561,732 B2 2/2020 Heyes et al.
10,583,084 B2 3/2020 Peer
10,653,780 B2 5/2020 Hope et al.
10,695,419 B2 6/2020 Ciaramella et al.
10,702,478 B2 7/2020 Guild et al.
10,780,052 B2 9/2020 DeRosa et al.
10,780,183 B2 9/2020 Heartlein et al.
10,821,186 B2 11/2020 Manoharan et al.
10,835,583 B2 11/2020 DeRosa et al.
10,857,105 B2 12/2020 Benenato et al.
10,920,246 B2 2/2021 Peer et al.
10,980,895 B2 4/2021 Payne et al.
11,066,355 B2 7/2021 Benenato et al.
11,084,779 B2 8/2021 Niitsu et al.
11,224,642 B2 1/2022 Heartlein et al.
11,278,611 B2 3/2022 Ciaramella et al.
11,865,190 B2 * 1/2024 Leavitt .................. C12N 15/111
11,980,673 B2 * 5/2024 Leavitt ................. A61K 38/465
2003/0077829 A1 4/2003 MacLachlan
2003/0125292 A1 7/2003 Semple et al.
2005/0118253 A1 6/2005 MacLachlan et al.
2005/0266067 A1 12/2005 Sengupta et al.
2006/0051405 A1 3/2006 MacLachlan et al.
2006/0057194 A1 3/2006 Gao
2006/0134189 A1 6/2006 MacLachlan et al.
2006/0257465 A1 11/2006 Maurer et al.
2007/0087045 A1 4/2007 Li et al.
2007/0218122 A1 9/2007 MacLachlan et al.
2008/0171716 A1 7/2008 MacLachlan et al.
2010/0041152 A1 2/2010 Wheeler et al.
2010/0239521 A1 9/2010 Mozafari
2010/0297242 A1 11/2010 Park et al.
2010/0330154 A1 12/2010 Panzne et al.
2011/0111044 A1 5/2011 Zhao et al.
2011/0229581 A1 9/2011 Zhao et al.
2011/0262527 A1 10/2011 Heyes et al.
2011/0305769 A1 12/2011 Zhao et al.
2012/0015026 A1 1/2012 Francese et al.
2012/0270921 A1 * 10/2012 de Fougerolles ....... A61P 31/14
435/375
2013/0156849 A1 6/2013 De Fougerolles et al.
2014/0161894 A1 6/2014 Maclachlan et al.
2014/0199374 A1 7/2014 Maurer et al.
2016/0022580 A1 1/2016 Ramsay et al.
2016/0106842 A1 * 4/2016 Baryza ...................... A61P 9/12
549/451
2016/0151284 A1 6/2016 Heyes et al.
2016/0228366 A1 * 8/2016 Ali ....................... A61K 31/542
2016/0289674 A1 10/2016 Bancel et al.
2016/0317647 A1 11/2016 Ciaramella

(56) References Cited

U.S. PATENT DOCUMENTS

2017/0143848 A1 5/2017 Calias et al.
2017/0240888 A1* 8/2017 Tremblay ............. C12N 15/113
2018/0085474 A1 3/2018 Almarsson et al.
2018/0153822 A1 6/2018 Karve et al.
2018/0200186 A1 7/2018 Chen et al.
2018/0263918 A1 9/2018 Derosa et al.
2018/0311176 A1 11/2018 Ozsolak et al.
2018/0318409 A1 11/2018 Valiante et al.
2018/0344638 A1 12/2018 Nam et al.
2018/0355417 A1* 12/2018 Shuber ..................... C12N 9/22
2019/0292130 A1 9/2019 Peer et al.
2019/0292566 A1 9/2019 Thomas et al.
2019/0298657 A1 10/2019 Martini et al.
2019/0307689 A1 10/2019 Ramsay et al.
2019/0336452 A1 11/2019 Brader
2019/0380963 A1 12/2019 Chen et al.
2020/0030408 A1 1/2020 Miller et al.
2020/0069599 A1 3/2020 Smith et al.
2020/0113830 A1 4/2020 Geall et al.
2020/0129445 A1 4/2020 Patel et al.
2020/0131498 A1 4/2020 Martini et al.
2020/0155706 A1 5/2020 De Fougerolles et al.
2020/0157157 A1 5/2020 Karve et al.
2020/0157540 A1 5/2020 Majeti et al.
2020/0163878 A1 5/2020 Baumhof et al.
2020/0172472 A1 6/2020 Du
2020/0224220 A1 7/2020 Finer et al.
2020/0297634 A1 9/2020 Karmali et al.
2020/0306191 A1 10/2020 Schariter et al.
2020/0330599 A1 10/2020 Goldys et al.
2020/0353062 A1 11/2020 Sammatur et al.
2020/0368173 A1 11/2020 Hatanaka et al.
2021/0002640 A1 1/2021 Kang et al.
2021/0009503 A1 1/2021 Derosa et al.
2021/0024907 A1 1/2021 Angel et al.
2021/0024928 A1 1/2021 Reebye et al.
2021/0046192 A1 2/2021 Karve et al.
2021/0115101 A1 4/2021 Bancel et al.
2021/0122702 A1 4/2021 Du
2021/0128474 A1 5/2021 Strodiot et al.
2021/0128485 A1 5/2021 Stephan
2021/0128488 A1 5/2021 Du
2021/0145746 A1 5/2021 Razavi et al.
2021/0145982 A1 5/2021 Hoge et al.
2021/0162052 A1 6/2021 Thomas et al.
2021/0170017 A1 6/2021 Lutz et al.
2021/0189397 A1 6/2021 Mirkin et al.
2021/0196820 A1 7/2021 Derosa et al.
2021/0198200 A1 7/2021 Benenato et al.
2021/0244665 A1 8/2021 Fisher et al.
2021/0275689 A1 9/2021 Karve et al.
2021/0284998 A1 9/2021 Thomas et al.
2021/0299244 A1 9/2021 Mosharraf et al.
2021/0315820 A1 10/2021 Ying et al.
2021/0346306 A1 11/2021 Dimitrov et al.
2021/0353554 A1 11/2021 Shah et al.
2021/0353556 A1 11/2021 Karve et al.
2021/0353761 A1 11/2021 Derosa et al.
2021/0378977 A1 12/2021 Karve et al.
2021/0378980 A1 12/2021 Horhota et al.
2022/0001029 A1 1/2022 Lam et al.
2022/0008338 A1 1/2022 Zhang et al.
2022/0016265 A1 1/2022 Androsavich et al.
2022/0023214 A1 1/2022 Marangoni
2022/0023442 A1 1/2022 Perez-garcia et al.
2022/0048867 A1 2/2022 Derosa et al.
2022/0049251 A1 2/2022 Harborth et al.
2022/0062175 A1 3/2022 Smith et al.
2022/0071905 A1 3/2022 Karve et al.
2022/0071916 A1 3/2022 Cheng et al.
2022/0072152 A1 3/2022 Askew et al.
2022/0072154 A1 3/2022 Heyes et al.

FOREIGN PATENT DOCUMENTS

WO 2012170930 A1 12/2012
WO 2013/004234 1/2013
WO 2014172045 10/2014
WO 2017201258 A1 11/2017
WO 2018107026 A1 6/2018
WO 2018213726 11/2018
WO WO-2018213726 A1 * 11/2018 .............. C12N 9/22
WO WO 2019089828 5/2019
WO WO 2019191780 10/2019
WO WO 2020023311 1/2020
WO WO 2020051243 3/2020
WO WO 2020056294 3/2020
WO WO 2020061367 3/2020
WO 2020077007 A1 4/2020
WO WO 2020097520 5/2020
WO WO 2020102172 5/2020
WO WO 2020142725 7/2020
WO WO 2020154705 7/2020
WO WO 2020154774 8/2020
WO WO 2020189773 9/2020
WO WO 2020210901 10/2020
WO WO 2020226960 11/2020
WO WO 2020227510 11/2020
WO WO 2020232276 11/2020
WO WO 2020252375 12/2020
WO WO 2020252589 12/2020
WO WO 2020254535 12/2020
WO WO 2021000041 1/2021
WO WO 2021021634 2/2021
WO WO 2021022008 2/2021
WO WO 2021022173 2/2021
WO WO 2021026358 2/2021
WO WO 2021028439 2/2021
WO WO 2021030701 2/2021
WO WO 2021038508 3/2021
WO WO 2021055660 3/2021
WO WO 2021081225 4/2021
WO WO 2021102411 5/2021
WO WO 2021108731 6/2021
WO WO 2021123399 6/2021
WO WO 2021138600 7/2021
WO WO 2021152115 8/2021
WO WO 2021155274 8/2021
WO WO 2021156267 8/2021
WO WO 2021159985 8/2021
WO WO 2021170034 9/2021
WO WO 2021195529 9/2021
WO WO 2021196659 10/2021
WO WO 2021207273 10/2021
WO WO 2021207630 10/2021
WO WO 2021214204 10/2021
WO WO 2021226463 11/2021
WO WO 2021226468 11/2021
WO WO 2021236479 11/2021
WO WO 2021236855 11/2021
WO WO 2021239880 12/2021
WO WO 2021243172 12/2021
WO WO 2022009052 1/2022
WO WO 2022015809 1/2022
WO WO 2022016089 1/2022
WO WO 2022018441 1/2022
WO WO 2022020534 1/2022
WO WO 2022032087 2/2022
WO WO 2022032154 2/2022
WO WO 2022040429 2/2022
WO WO 2022043551 3/2022
WO WO 2022046919 3/2022
WO WO 2022051866 3/2022

OTHER PUBLICATIONS

Suresh Rewar. “A systematic review on Parkinson’s disease (PD).” Indian Journal of Research in Pharmacy and Biotechnoogy, vol. 3(2), Mar.-Apr. 2015, pp. 176-185. (Year: 2015).*

(56) References Cited

OTHER PUBLICATIONS

Linde Schoenmaker et al. "mRNA-lipid nanoparticle COVID-19 vaccines: Structure and stability." International Journal of Pharmaceutics, vol. 601, 2021, Article 120586, pp. 1-13. (Year: 2021).*

Concetta Avitabile et al. "Incorporation of Naked Peptide Nucleic Acids into Liposomes Leads to Fast and Efficient Delivery." Bioconjugate Chemistry, vol. 26, 2015, pp. 1533-1541. (Year: 2015).

Daniel Zucker, David Marcus, Yechezkel Barenholz, and Amiram Goldblum. "Liposome drugs' loading efficiency: A working model V based on loading conditions and drug's physicochemical properties." Journal of Controlled Release, vol. 139, 2009, pp. 73-80. (Year: 2009).

DH Ripin and DA Evans. https://organicchemistrydata.org/hansreich/resources/pka/pka_data/evans_pKa_table.pdf accessed Jul. 17, 2023, originally published Apr. 8, 2022, pp. 1-6. (Year: 2022).

Gokce Engudar et al. "Remote loading of liposomes with a 1241-radioiodinated compound and their in vivo evaluation by PET/CT in a murine tumor model." Theranostics, vol. 8, Issue 21, 2018, pp. 5828-5841. (Year: 2018).

Jayesh A. Kulkarni et al. "On the Formation and Morphology of Lipid Nanoparticles Containing Ionizable Cationic Lipids and siRNA." ACS Nano, vol. 12, 2018, pp. 4787-4795, published Apr. 3, 2018. (Year: 2018).

Mackensie C. Smith, Rachael M. Crist, Jeffrey D. Clogston1, and Scott E. McNeil. "Zeta potential: a case study of cationic, anionic, and neutral liposomes." Analytical and Bioanalytical Chemistry, vol. 409, 2017, pp. 5779-5787. (Year: 2017).

Manuel J. Carrasco et al. "Ionization and structural properties of mRNA lipid nanoparticles influence expression in intramuscular and intravascular administration." Communications Biology, vol. 4:956, 2021, pp. 1-15. (Year: 2021).

Maria Laura Immordino, Franco Dosio, and Luigi Cattel. "Stealth liposomes: review of the basic science, rationale, and clinical applications, existing and potential." International Journal of Nanomedicine, vol. 1 (3), 2006, pp. 297-315. (Year: 2006).

Rebecca L. Ball, Khalid A. Hajj, Jamie Vizelman, Palak Bajaj, and Kathryn A. Whitehead. "Lipid Nanoparticle Formulations for Enhanced Co-delivery of siRNA and mRNA." Nano Letters, vol. 18, 2018, pp. 3814-3822 and 12 pages of supporting info, published Apr. 25, 2018 (Year: 2018).

Surojit Sur, Anja C. Fries, Kenneth W. Kinzler, Shibin Zhou, and Bert Vogelstein. "Remote loading of preencapsulated drugs into stealth liposomes." Proceedings of the National Academy of Sciences, vol. 111 No. 6, Feb. 11, 2014, pp. 2283-2288 (Year: 2014).

Feigner et al. "Lipofection: A highly efficient, lipid-mediated DNA-transfection procedure." Proceedings of the National Academy of Sciences USA, vol. 84, Nov. 1987, pp. 7413-7417. (Year: 1987).

Inglut et al. "Immunological and Toxicological Considerations for the Design of Liposomes." Nanomaterials, vol. 10, 190, 2020, pp. 1-24. (Year: 2020).

Shannon Weiman. "The Evolution of Lipid Nanoparticles: From Biophysics to Gene Therapy, Vaccines and Drug Delivery." https:/keypoint.keystonesymposia.org/home/the-evol ution-of-li pid-nanoparticles-from-biophysics-to-gene-therapy-vaccines-and-drug-delivery, pp. 1-20. (Year: 2022).

Derek Lowe. "RNA Vaccines And Their Lipids." https://www.science.org/contenUblog-post/rna-vaccines-and-their-lipids accessed Oct. 19, 2022, originally published Jan. 11, 2021, pp. 1-15. (Year: 2021).

Sanket Shah, Vivek Dhawanb, Rene Holm, Mangal S. Nagarsenker, Yvonne Perrie. "Liposomes: Advancements and innovation in the manufacturing process." Advanced Drug Delivery Reviews, vol. 154-155, 2020, pp. 102-122. (Year: 2020).

Kulkarni, Jayesh A et al. Â•on the Formation and Morphology of Lipid Nanoparticles Containing Ionizable Cationic Lipid and siRNA. ACS nano vol. 12,5 (2018): 4787-4795. doi:10.1021/acsnano.8b01516.

Simberg, Dmitri et al. "DOT AP (and other cationic lipids): chemistry, biophysics, and transfection." Critical reviews in therapeutic drug carrier systems vol. 21,4 (2004): 257-317. doi: 10.1615/critrevtherdrugcarriersyst.v21.i4.10 Abstract Only.

Leung AK, Tam YY, Cullis PR. Lipid nanoparticles for short interfering RNA delivery. Advances in genetics. Jan. 1, 2014;88:71-110.

Morrissey DV, Lockridge JA, Shaw L, Blanchard K, Jensen K, Breen W, Hartsough K, Machemer L, Radka S, Jadhav V, Vaish N. Potent and persistent in vivo anti-HBV activity of chemically modified siRNAs. Nature biotechnology. Aug. 1, 2005;23(8):1002-7.

Zimmermann TS, Lee AC, Akinc A, Bramlage B, Bumcrot D, Fedoruk MN, Harborth J, Heyes JA, Jeffs LB, John M, Judge AD. RNAi-mediated gene silencing in non-human primates. Nature. May 4, 2006;441(7089):111-4.

Basha G, Novobrantseva TI, Rosin N, Tam YY, Hafez IM, Wong MK, Sugo T, Ruda VM, Qin J, Klebanov B, Ciufolini M. Influence of cationic lipid composition on gene silencing properties of lipid nanoparticle formulations of siRNA in antigen-presenting cells. Molecular Therapy. Dec. 1, 2011;19(12):2186-200.

Novobrantseva TI, Borodovsky A, Wong J, Klebanov B, Zafari M, Yucius K, Querbes W, Ge P, Ruda VM, Milstein S, Speciner L. Systemic RNAi-mediated gene silencing in nonhuman primate and rodent myeloid cells. Molecular Therapy-Nucleic Acids. Jan. 1, 2012;1:e4.

Jayaraman M, Ansell SM, Mui BL, Tam YK, Chen J, Du X, Butler D, Eltepu L, Matsuda S, Narayanannair JK, Rajeev KG. Maximizing the potency of siRNA lipid nanoparticles for hepatic gene silencing in vivo. Angewandte Chemie. Aug. 20, 2012;124(34):8657-61.

Port F, Bullock SL. Expansion of the CRISPR toolbox in an animal with tRNA-flanked Cas9 and Cpf1 gRNAs. BioRxiv. Mar. 31, 2016:046417.

Hur JK, Kim K, Been KW, Baek G, Ye S, Hur JW, Ryu SM, Lee YS, Kim JS. Targeted mutagenesis in mice by electroporation of Cpf1 ribonucleoproteins. Nature biotechnology. Aug. 2016;34(8):807-8.

Kim D, Kim J, Hur JK, Been KW, Yoon SH, Kim JS. Genome-wide analysis reveals specificities of Cpf1 endonucleases in human cells. Nature biotechnology. Aug. 2016;34(8):863-8.

Kulkarni JA, Cullis PR, Van Der Meel R. Lipid nanoparticles enabling gene therapies: from concepts to clinical utility. Nucleic acid therapeutics. Jun. 1, 2018;28(3):146-57.

Wei T, Cheng Q, Min YL, Olson EN, Siegwart DJ. Systemic nanoparticle delivery of CRISPR-Cas9 ribonucleoproteins for effective tissue specific genome editing. Nature communications. Jun. 26, 2020;11(1):3232.

Kulkarni JA, Thomson SB, Zaifman J, Leung J, Wagner PK, Hill A, Tam YY, Cullis PR, Petkau TL, Leavitt BR. Spontaneous, solvent-free entrapment of siRNA within lipid nanoparticles. Nanoscale. 2020;12(47):23959-66.

Hou X, Zaks T, Langer R, Dong Y. Lipid nanoparticles for mRNA delivery. Nature Reviews Materials. Dec. 2021;6(12):1078-94.

Semple SC, Klimuk SK, Harasym TO, Dos Santos N, Ansell SM, Wong KF, Maurer N, Stark H, Cullis PR, Hope MJ, Scherrer P. Efficient encapsulation of antisense oligonucleotides in lipid vesicles using ionizable aminolipids: formation of novel small multilamellar vesicle structures. Biochimica et Biophysica Acta (BBA)—Biomembranes. Feb. 9, 2001;1510(1-2):152-66.

Maurer N, Wong KF, Stark H, Louie L, McIntosh D, Wong T, Scherrer P, Semple SC, Cullis PR. Spontaneous entrapment of polynucleotides upon electrostatic interaction with ethanol-destabilized cationic liposomes. Biophysical Journal. May 1, 2001;80(5):2310-26.

Ambegia E, Ansell S, Cullis P, Heyes J, Palmer L, MacLachlan I. Stabilized plasmid-lipid particles containing PEG-diacylglycerols exhibit extended circulation lifetimes and tumor selective gene expression. Biochimica et Biophysica Acta (BBA)—Biomembranes. May 20, 2005;1669(2):155-63.

Jeffs LB, Palmer LR, Ambegia EG, Giesbrecht C, Ewanick S, MacLachlan I. A scalable, extrusion-free method for efficient liposomal encapsulation of plasmid DNA. Pharmaceutical research. Mar. 2005;22(3):362-72.

(56) References Cited

OTHER PUBLICATIONS

Judge A, McClintock K, Phelps JR, MacLachlan I. Hypersensitivity and loss of disease site targeting caused by antibody responses to PEGylated liposomes. Molecular Therapy. Feb. 1, 2006;13(2):328-37.

Wilson KD, Raney SG, Sekirov L, Chikh G, dejong SD, Cullis PR, Tam YK. Effects of intravenous and subcutaneous administration on the pharmacokinetics, biodistribution, cellular uptake and immunostimulatory activity of CpG ODN encapsulated in liposomal nanoparticles. International immunopharmacology. Aug. 1, 2007;7(8):1064-75.

De Jong S, Chikh G, Sekirov L, Raney S, Semple S, Klimuk S, Yuan N, Hope M, Cullis P, Tam Y. Encapsulation in liposomal nanoparticles enhances the immunostimulatory, adjuvant and anti-tumor activity of subcutaneously administered CpG ODN. Cancer Immunology, Immunotherapy. Aug. 2007;56(8):1251-64.

Raney SG, Wilson KD, Sekirov L, Chikh G, De Jong SD, Cullis PR, Tam YK. The effect of circulation lifetime and drug-to-lipid ratio of intravenously administered lipid nanoparticles on the biodistribution and immunostimulatory activity of encapsulated CpG-ODN. Journal of drug targeting. Jan. 1, 2008;16(7-8):564-77.

Wang M, Zuris JA, Meng F, Rees H, Sun S, Deng P, Han Y, Gao X, Pouli D, Wu Q, Georgakoudi I. Efficient delivery of genome-editing proteins using bioreducible lipid nanoparticles. Proceedings of the National Academy of Sciences. Mar. 15, 2016;113(11):2868-73.

Wang et al. "Supporting Information." Proceedings of the National Academy of Sciences. Suppl. Mar. 15, 2016;113(11):pp. 1-6.

Yin H, Song CQ, Suresh S, Wu Q, Walsh S, Rhym LH, Mintzer E, Bolukbasi MF, Zhu LJ, Kauffman K, Mou H. Structure-guided chemical modification of guide RNA enables potent non-viral in vivo genome editing. Nature biotechnology. Dec. 2017;35(12):1179-87 (22 pages).

Evers MJ, Kulkarni JA, van der Meel R, Cullis PR, Vader P, Schiffelers RM. State-of-the-art design and rapid-mixing production techniques of lipid nanoparticles for nucleic acid delivery. Small Methods. Sep. 2018;2(9):1700375.

Cullis, Pieter R. et al., "Lipid Nanoparticle Systems for Enabling Gene Therapies", Molecular Therapy, vol. 25, No. 17, 2017, pp. 1467-1475.

Dalby, Brian et al., "Advancced transfection with Lipofectamine 2000 reagent: primary neurons, siRNA, and high-throughput applications", Methods 33 (2004), pp. 95-103.

Heyes, James et al., "Lipidd Encapsulation Enables the Effective Systemic Delivery of Polyplex Plasmid DNA", Molecular Therapy, vol. 15, No. 4, Apr. 2007, pp. 713-720.

International Search Report for International Application No. PCT/US2019-055472, dated Feb. 3, 2020, 4 pages.

Kastner, Elizabeth et al., "High-throughput manufacturing of size-tuned liposomes by a new microfluidics using enhanced statistical tools for characterization", International Journal of Pharmaceutics, 477 (2015), pp. 361-368.

Kim, Dongbum et al., "Adjuvant effect of liposomes-encapsulated natural phosphodiester CpG-DNA", http://dx.doi.org/10.5483/BMBRep.2011.44.11.758, pp. 758-763.

Kulkarni, Jayesh A. et al., "Lipid Nanoparticles Enabling Gene Therapies: From Concepts to Clinical Utility", Nucleic Acid Therapies, vol. 28, No. 3, (2018), pp. 146-157.

Mortazavi, S. Moazam et al., "Preparation of liposomal gene therapy vectors by a scalable method without using volatile solvents or detergents", Journal of Biotechnology 129 (2007), 604-613.

Mozafari, M.R. et al., "Cytotoxicity evaluation of anionic nanoliposomes and nanolipoplexes prepared by the heating method without employing volatile solvents and detergents", Pharmazie 62:3 (2007), 205-209.

Reitwyk, Stephanie et al., "Next-Generation Lipids in RNA Interference Therapeutics", ACS Nano 2017, 11, 7572-7586.

Written Opinion in International Application No. PCT/US2019/055472, mailed Feb. 3, 2020, 6 pages.

Yu, Bo et al., "Microfluid Assembly of Lipid-based Oligonucleotide Nanoparticles", Anticancer Research 31 (2011), pp. 771-776.

* cited by examiner

Untreated Control

TCV Delivery of RNP

COMPOSITIONS AND SYSTEMS COMPRISING TRANSFECTION-COMPETENT VESICLES FREE OF ORGANIC-SOLVENTS AND DETERGENTS AND METHODS RELATED THERETO

CROSS-REFERENCE TO RELATED APPLICATIONS

This application is a divisional of U.S. application Ser. No. 17/281,678 filed Mar. 31, 2021 which is a 371 National Stage of Int'l Appl. No. PCT/US2019/055472, filed Oct. 9, 2019, which claims benefit of priority to U.S. Provisional Patent Application Ser. No. 62/743,116, filed Oct. 9, 2018, each and all of which are incorporated herein by reference in their entireties.

BACKGROUND

One of the important areas for scientific research and medical treatments is the desire to selectively and efficiently deliver RNA, DNA, other nucleic acids and/or protein cargo to target sites such as specific target cells. This can be helpful for a variety of reasons including improved patient treatments such as gene therapy and for treatment of cancer and other conditions. For example, gene therapy can possibly be used in the brain and throughout the central nervous system to treat some of the classic horrible neurological disorders that humans may suffer, such as Alzheimer's disease, Parkinson's disease, Huntington's disease, frontotemporal dementia, amyotrophic lateral sclerosis, spinal muscular atrophy, and more. Current gene therapy approaches have several problems with their widespread application, especially for human patients, for example because of the need for repeated dosing and toxicity of packaging that carries therapeutic nucleic acids into the patient. The current compositions, methods, etc., herein help remedy one or more of these or other such problems.

Turning to a more scientific discussion of the delivery of DNA and other nucleic acids into target sites such as diseased cells in the brain, existing methods for such delivery include lipid particles, in some cases called lipid nanoparticles ("LNPs") or liposomes. The term lipid nanoparticles or "LNPs" is used to describe lipid-based particles at about neutral pH that typically contain nucleic acid and have an electron dense core. Liposomes, also known as vesicles, are lipid-based structures with a single bilayer and an aqueous core. Typical established processes of LNP formation load the vesicle with specific cargo at time of initial vesicle formation. These processes further use specialized instrumentation, organic solvents and/or detergents, require large amounts of material, and constitute processing times on the order of days, all of which severely hamper utility, accessibility and therapeutic usability.

LNPs and other lipid particles typically comprise an ionizable cationic lipid, one or more phospholipid(s), cholesterol (Chol), and polyethyleneglycol-lipid (PEG-lipid) (Maurer, Wong et al. 2001; Semple, Klimuk et al. 2001; Semple, Akinc et al. 2010; Belliveau, Huft et al. 2012; Leung, Hafez et al. 2012; Suhr, Coelho et al. 2015). (Various references are set forth herein that discuss certain systems, apparatus, methods and other information; all such references are incorporated herein by reference in their entirety and for all their teachings and disclosures, regardless of where the references may appear in this application. Citation to a reference herein is not an admission that such reference constitutes prior art to the current application.) An example of an LNP composition is the combination of ionizable cationic lipids, phospholipids, cholesterol and polyethylene glycol (PEG)-lipid at a ratio of 50/10/38.5/1.5 mol % (respectively). This composition has been shown to display potent hepatocyte gene silencing (siRNA) or expression (mRNA) following intravenous administration (Semple, Akinc et al. 2010; Jayaraman, Ansell et al. 2012; Pardi, Tuyishime et al. 2015; Suhr, Coelho et al. 2015). Others have described LNP compositions comprised of ionizable cationic lipids, phospholipids, cholesterol and polyethylene glycol (PEG)-lipid at a ratio 50/10/38.5/1.5 molar % as siRNA delivery of primary neuronal cells in culture and for delivery to the brain (Rungta, Choi et al. 2013).

LNP formulations can be generated through rapid-mixing of the lipid components dissolved in ethanol with an acidic aqueous phase consisting of the nucleic acid cargo (Jeffs, Palmer et al. 2005; Belliveau, Huft et al. 2012; Leung, Hafez et al. 2012). An established rapid-mixing process for LNP manufacture includes microfluidic mixing through a staggered herringbone micromixer (SHM) (Belliveau, Huft et al. 2012; Rungta, Choi et al. 2013; Leung, Tam et al. 2015), or T-junction mixing with specialized pumps (Jeffs, Palmer et al. 2005) or a more dated approach of ethanol-/detergent-destabilised loading of pre-formed vesicles (Wheeler, Palmer et al. 1999; Tam, Monck et al. 2000; Maurer, Wong et al. 2001; Semple, Klimuk et al. 2001). In all three methods, an ethanolic solution (or detergent) is required to provide sufficient membrane fluidity for lipid reorganization and entrapment to occur, and in the case of the SHM and T-junction techniques, particle formation also occurs upon dilution of the ethanolic solution into the aqueous phase (Belliveau, Huft et al. 2012; Zhigaltsev, Belliveau et al. 2012; Zhigaltsev, Tam et al. 2016). However, the resulting suspension is not "ready-to-use" due to the organic solvent and acidic pH and thus the resulting suspension requires substantial downstream processing. In terms of material costs and time, these approaches have significant impediments to achieving a transfection-competent formulation at lab-scales for in vitro applications or for or therapeutic levels for direct administration.

There remains a need for transfection reagents that effectively deliver nucleic acid and protein cargo into mammalian cells in a non-toxic manner, including for cultured mammalian primary cells (generally, primary cells are non-transformed, non-immortalized cells obtained directly from a target tissue). While the importance of using primary cells and their advantages over the use of cell lines is well-understood, the difficulty encountered in transfecting such cells has precluded their use almost entirely from any type of discovery or validation studies requiring selective gene knockdown. Furthermore, a move towards personalized medicine is pushing for functional genomic screening and validation to be done in primary patient cells, increasing the need for robust and non-toxic transfection methods for these hard-to-transfect cell types.

The present systems and methods, etc., provide solutions to one or more of these difficulties and/or provide other advantages.

SUMMARY

The systems, compositions, devices and methods, etc., herein provide lipid-based vesicles, typically herein called transfection competent vesicles (TCVs), configured to safely and efficiently deliver proteins, ribonucleoproteins (RNPs), RNA, DNA, and other nucleic acid cargoes and other selected cargoes into target cells. The safety and efficiency are each, and both, achieved in part by eliminating destabilizing agents such as organic solvents such as ethanol and detergents such as sodium dodecyl sulfate from the TCV loading processes (i.e., inserting a selected cargo into the TCV), TCV storage processes, and/or TCV delivery processes. Thus, the TCV are maintained in a destabilizing agent-free solution, for example as a destabilizing agent-free suspension.

As used herein, a TCV is a type of liposome or other vesicle that is lipid-based and is generated and/or stored without destabilizing agents and without a selected cargo inside. One advantage of such TCVs is that they can be stored in solution or as a suspension without the presence of destabilizing agents, can entrap selected cargos without the presence or of destabilizing agents, and can deliver such selected cargos to target cells without the presence of destabilizing agents. Selected cargo indicates RNPs, RNAs, DNAs, proteins, etc., that create a desired effect on a target cell and/or target patient that is transfected with the TCV containing the selected cargo. Thus, unless otherwise clear from the context, the TCVs herein lack the ultimately selected cargo, and in certain embodiments are empty other than ambient solution or the like. Such TCVs are configured to safely and efficiently deliver nucleic acid and protein cargo, etc., into mammalian cells without the use of organic solvents or other destabilising agents.

TCV delivery processes can comprise transfection of mammalian cells such as primary cells with the selected cargo. The cargoes can also comprise nucleic acids complexed with a protein, such as a ribonucleoprotein (RNP). The systems, compositions, devices and methods, etc., herein, in some embodiments, can provide empty TCVs or loaded TCVs.

In some aspects, the systems, compositions, devices and methods, etc., herein provide the transfection-competent vesicles (TCVs) without organic solvents and other destabilising agents that have previously been required to entrap (or load) cargo into lipid vesicles or liposomes and/or to store such vesicles. The compositions, methods, etc., herein can be used or performed without the use of specialized instruments, for example the pre-formed TCVs herein can be loaded by gently mixing the empty TCV-containing suspension with various types of selected cargo via reciprocation of a pipette. The compositions, methods, etc., herein can be particularly useful for "bench-top loading", and can be used with small or large amounts of selected cargo material. In addition, a single batch of empty TCVs can be bench-top loaded with multiple different selected cargos in parallel.

In some embodiments, the systems, compositions, devices and methods, etc., herein provide empty TCVs that are organic solvent-free and detergent-free. If ethanol or detergent or other destabilizing agent has been used to generate TCVs, it is removed via dialysis or other suitable method to provide an organic solvent-free, detergent-free TCV composition. The TCVs may be loaded using gentle mixing such as repeated manual reciprocation of the TCV-generating fluid in a pipette, SHM, T-junction mixing or extrusion methods, or other TCV-mixing methods as desired.

In one aspect, the lipid-based TCVs are comprised of a mixture of an ionizable cationic lipid, phospholipid, cholesterol and PEG-lipid, and the TCV-containing composition is organic-solvent and/or detergent free, which terminology is used in its normal usage to indicate that such organic-solvent and detergent are essentially absent such that no significant deleterious effects are caused by the organic-solvent and/or detergent although minor, trace quantities may remain in the composition.

In some aspects, the ionizable cationic lipid comprises between 20-50% of the lipid component of the TCVs. In one aspect, the empty lipid-based TCVs contain lipid components in a ratio of DODMA/DOPE/DSPC/Chol/PEG-lipid at 20/30/10/39/1 mol %. In another aspect, the empty lipid-based TCVs contain lipid components in a ratio of DODMA/DOPE/DSPC/Chol at 20/30/10/40 mol %. In another aspect, the empty lipid-based TCVs contain lipid components in a ratio of DODMA/DSPC/Chol/PEG-lipid at 50/10/39/1 mol %. In another aspect, the empty lipid-based TCVs contain lipid components in a ratio of DODMA/DOPE/DSPC/Chol at 50/10/39/1 mol %. Additional ranges of components can also be used as desired. In certain aspects, the ratio of ionizable cationic lipid is reduced. For example, the ratio of ionizable cationic lipid can be about 10 mol %, 20 mol %, 30 mol %, 40 mol %, 50 mol % or 60 mol %.

In one aspect, the empty lipid-based TCVs is mixed with the nucleic acid selected cargo for 5 seconds, 10 seconds, 15 seconds, 20 seconds, 30 seconds, 45 seconds, 1 minute or 2 minutes as desired, for example 10-30 seconds. The organic solvent-free, detergent-free TCVs can then be stored in an organic solvent-free, detergent-free environment and/or administered to target cells such as mammalian cells again in an in an organic solvent-free, detergent-free environment.

In some aspects, the nucleic acid selected cargo can be double strand DNA, single strand DNA, RNA, small interfering RNA, short hairpin RNA, messenger RNA, complementary DNA, microRNA, plasmid DNA, or a combination thereof. In some aspects, the nucleic acid selected cargo may comprise synthetic or chemically modified oligonucleotides, for example to improve the stability of the selected cargo. The selected cargo can be a protein that is complexed with a nucleic acid (PNA). The protein selected cargo may be proteins involved in gene-editing or proteins that function as reporters for cell labelling (such as fluorescent markers and the like). In some embodiments, the protein-based selected cargo that is complexed with a nucleic acid is a ribonucleoprotein.

In some aspects, the present systems, devices and methods, etc., provide methods of encapsulating a selected cargo into a lipid-based transfection competent vesicle (TCV) comprising:

- providing a water-based solution comprising the lipid-based TCV, The water-based solution can be free of destabilizing agents; and,
- mixing the selected cargo into the solution under conditions suitable and for a time sufficient for the selected cargo to encapsulate within the lipid-based TCV to provide a lipid-based TCV-encapsulated selected cargo, The mixing can be performed without the presence of an organic solvent or detergent.

The destabilizing agent can be at least one of an organic solvent or a detergent. The organic solvent can be, for example, methanol, isopropyl alcohol, tetrahydrofuran (THF), dimethylsulphoxide (DMSO), dimethylformamide (DMF), or acetonitrile (ACN). The detergent can be, for example, sodium dodecyl sulfate (SDS). The destabilising agent can be temperature. The water-based solution can be a 25 mM to 100 mM acetate buffer.

The lipid-based TCV can be empty prior to the encapsulation, and the methods further can comprise:

- obtaining the lipid-based TCV-encapsulated selected cargo in a water-based solution substantially free of solvent and detergents.

The lipid-based TCV can comprise a cationic lipid, such as an ionizable cationic lipid. The lipid-based TCV can comprise about 20 mol % to 50 mol % cationic lipid. The ionizable cationic lipid can comprise 1,2-Dioleyloxy-3-dimethylamino-propane (DODMA). The lipid-based TCV can comprise a mixture of 1,2-Dioleyloxy-3-dimethylamino-propane (DODMA), 1,2-diolcoyl-sn-glycero-3-phosphocholine (DOPC), 1,2-dioleoyl-sn-glycero-3-phosphoethanolamine (DOPE), and 1,2-distearoyl-sn-glycero-3-phosphocholine (DSPC). The mixture further can comprise at least one of polyethylene glycol (PEG) or cholesterol.

The lipid-based TCV can comprise a mixture of DODMA/DOPE/DSPC/Chol/PEG-lipid at about 20/30/10/39/1 mol %, can comprise a mixture of DODMA/DOPE/DSPC/Chol at about 20/30/10/40 mol %, a mixture of DODMA/DSPC/Chol at about 50/10/40 mol %, a mixture of DODMA/DSPC/Chol/PEG-lipid at about 50/10/39/1 mol %, or a mixture of DODMA/DSPC/Chol/PEG at about 50/10/39/1 mol %.

The selected cargo can be a nucleic acid, such as a modified nucleic acid. The modified nucleic acid can comprise, for example, at least one of 2'-O-Methylation (2'-O-ME), phosphorothioate, or morpholino, a locked nucleic acid. The nucleic acid can be a deoxyribonucleic acid (DNA). The DNA can comprise a double strand DNA, a single strand DNA, a complementary DNA (cDNA) or a plasmid DNA. The nucleic acid can comprise a ribonucleic acid (RNA). The RNA can comprise a small interfering RNA (siRNA), short hairpin RNA, a messenger RNA (mRNA), a microRNA (miRNA). The selected cargo can comprise a protein. The protein can be part of a ribonucleoprotein (RNP), which can be a functional ribonucleoprotein. The RNP can comprise at least one of a Cas9 protein or a guide RNA, both a Cas9 protein and a guide RNA, or comprise a Cas9 protein and a guide RNA and a single stranded DNA (ssDNA).

The cargo can comprise at least one of an enzyme, a nuclease, and endonuclease, or a primer. The cargo can comprise at least one of zinc finger nuclease (ZFN), TALEN, Cas9, Cas10, Cas11, Cas12, or Cpf1. The cargo can comprise at least one of an enzyme, a nuclease, and endonuclease, or a primer. The cargo can comprise an mRNA encoding for a nuclease or an antigen.

The methods further can comprise mixing the lipid-based TCV with the selected cargo, The selected cargo can be a nucleic acid that can be present at a ratio of about 0.022-0.058 mg selected cargo per μmole cationic lipid. The methods further can comprise mixing the lipid-based TCV with the selected cargo, The selected cargo can be a nucleic acid that can be present at a ratio of about 0.029-0.116 mg selected cargo per μmole cationic lipid. The lipid-based TCV and the selected cargo can be mixed at an about 467 molar ratio of lipid-based TCV: selected cargo. The selected cargo can be a ribonucleoprotein (RNP). The lipid-based TCV and the selected cargo can be mixed at an about 400 to 1200 molar ratio of lipid-based TCV: selected cargo. The lipid-based TCV and the selected cargo can be mixed at an about 473 to 1173 molar ratio of lipid-based TCV:selected cargo. The lipid-based TCV and the selected cargo can be mixed at a ratio up to about 3000 to 5000 molar ratio of lipid-based TCV:selected cargo.

The lipid-based TCV and the selected cargo can be mixed at about room temperature for about 10 to 15 seconds, or for about 10 to 30 seconds. The mixing can be performed using staggered herringbone micromixing or T-junction mixing. The mixing can be performed via reciprocation in a pipette.

In some aspects, the present systems, devices and methods, etc., provide compositions comprising a lipid-based transfection competent vesicle (TCV) in a water-based solution The compositions can be free of destabilizing agents organic solvents and detergents. The composition and/or lipid-based TCV can be further be configured as discussed in the Summary, the Figures, the Detailed Description or the Claims. The present systems, devices and methods, etc., provide compositions comprising a lipid-based transfection competent vesicle (TCV)-encapsulated selected cargo in a water-based solution substantially free of destabilizing agents such as organic solvents and detergents The lipid-based TCV-encapsulated selected cargo as discussed herein.

The present systems, devices and methods, etc., also provide methods of transfection, the methods comprising transfecting a target cell with a lipid-based transfection competent vesicle (TCV)-encapsulated selected cargo as discussed herein. The target cell can be a mammalian cell, such as a mammalian primary cell, a mammalian primary neuronal cell, a cultured mammalian cell, or a cell from a mammalian patient.

The methods herein can be performed in a laboratory, for example for bench-top loading. The methods can be performed in a factory to produce commercial quantities of transfected cells. The methods can be performed as a part of an in vivo procedure, a medical procedure, a therapeutic procedure or a gene therapy procedure. The methods can be performed as a part of treating Alzheimer's disease, Parkinson's disease, Huntington's disease, frontotemporal dementia, amyotrophic lateral sclerosis, or spinal muscular atrophy. The methods further can comprise delivering the lipid-based TCV-encapsulated selected cargo to a brain of the patient.

In some further aspects, the present systems, devices and methods, etc., provide kits comprising the compositions herein. The compositions can be in a vessel and the kits can comprise instructions for use of the compositions. The instructions can direct use of the compositions according to any of the methods herein. The vessel can be configured to administer at least one dose of the compositions to a mammal, the kit further comprising at least one label comprising instructions for the administration.

In some aspects, the present systems, devices and methods, etc., provide isolated and purified compositions herein for use in the manufacture of a medicament for inhibiting, preventing, or treating a disease or condition in a patient, which can be a mammal.

These and other aspects, features and embodiments are set forth within this application, including the following Detailed Description and attached drawings. Unless expressly stated otherwise, all embodiments, aspects, features, etc., can be mixed and matched, combined and permuted in any desired manner. In addition, various references are set forth herein, including in the Cross-Reference To Related Applications, that discuss certain systems, apparatus, methods and other information; all such references are incorporated herein by reference in their entirety and for all their teachings and disclosures, regardless of where the references may appear in this application.

BRIEF DESCRIPTION OF THE DRAWINGS

FIGS. 4A, 4B. Incorporation of DOPE in an organic solvent-free, detergent-free empty TCV does not change TCV morphology. Cryo-TEM analysis was performed on TCVs of (A) DODMA/DOPE/DSPC/Chol/PEG-lipid at 20/30/10/39/1 mol % (DOPE=1,2-dioleoyl-sn-glycero-3-phosphoethanolamine; DSPC=1,2-distearoyl-sn-glycero-3-phosphocholine; PEG=polyethylene glycol), and (B) DODMA/DSPC/Chol/PEG-lipid (50/10/39/1 mol %). Scale bar=100 nm.

DETAILED DESCRIPTION

Figure 1:
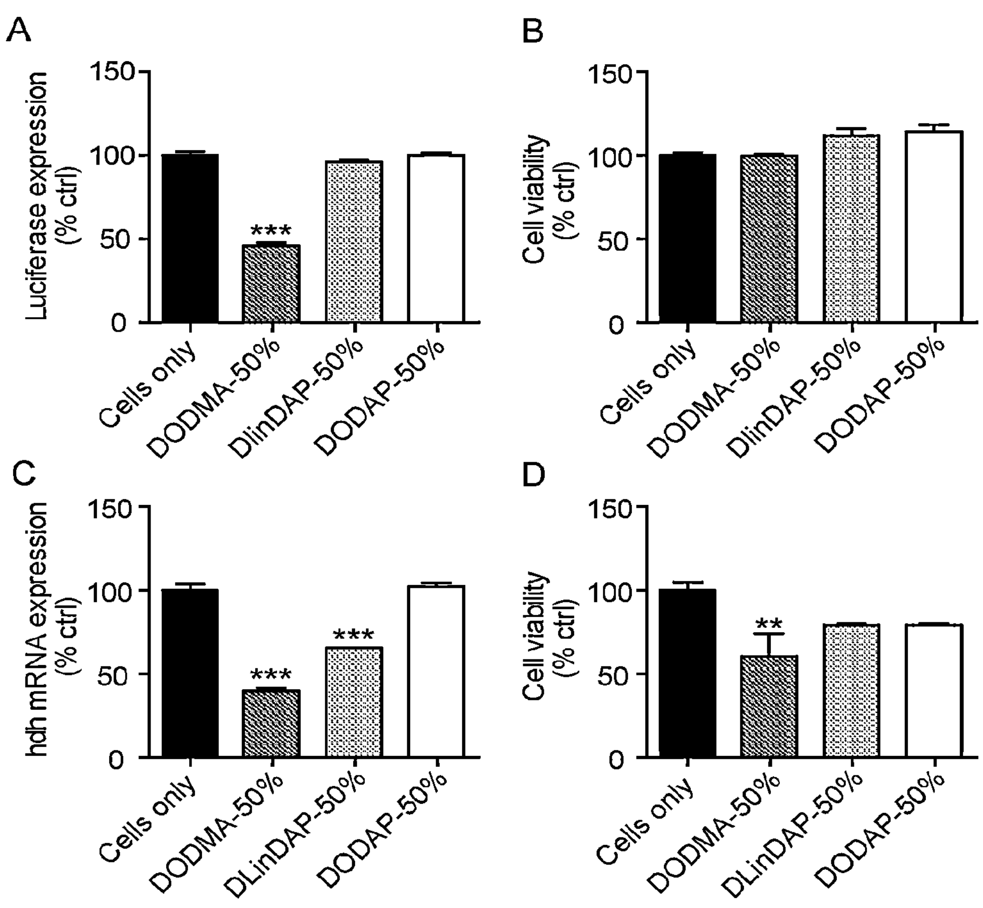
FIGS. 1A-1D. Transfection-competent vesicles (TCVs) produced according to the methods herein display knockdown in immortalized cells and primary neurons. (A) Relative luciferase expression in HEK-Luc cells after transfection with organic solvent-free, detergent-free TCVs composed of 50% ionizable cationic lipid. (B) Cell viability from the same set of transfections presented in (A) as % of control (cells only) wells. (C) Relative expression of hdh mRNA in primary cortical neurons after organic solvent-free, detergent-free TCV-mediated transfection of an siRNA selected cargo into the neurons. The siRNA targeted hdh, and the TCV were produced using the same panel of ionizable cationic lipids presented in 1(A). (D) Cell viability as measured by MTT reduction for an equivalent set of transfections in primary cortical neurons using organic solvent-free, detergent-free TCVs to deliver an off-target (luciferase) siRNA. N=4 per condition for HEK-Luc cells, N=3 wells per condition for primary neurons. Data represent the mean±SEM. *p<0.05, p<0.01, *p<0.001 by Bonforroni post-hoc analysis after a one-way ANOVA with each condition compared to the control (cells only) condition.

The systems, compositions, devices and methods, etc., herein provide lipid-based vesicles, typically herein called transfection competent vesicles (TCVs), configured to safely and efficiently deliver DNA and other nucleic acid selected cargoes into target cells. The safety and efficiency are each, and both, achieved in part by eliminating disrupting agents such as organic solvents such as ethanol and detergents such as sodium dodecyl sulfate from the TCV loading and storage processes (i.e., inserting a selected cargo into the TCV), and/or TCV delivery processes. TCV delivery processes can comprise transfection of mammalian cells such as primary cells with the selected cargo. The selected cargoes can also comprise nucleic acids complexed with a protein, such as a ribonucleoprotein (RNP).

In some embodiments, the systems, compositions, devices and methods, etc., herein provide empty lipid-based TCVs that are organic solvent-free and detergent-free. The loaded TCVs may be generated using gentle mixing such as repeated manual reciprocation of the TCV-generating fluid in a pipette, SHM, T-junction mixing or extrusion methods, or other TCV-mixing methods as desired.

In one aspect, the lipid-based TCVs are comprised of a mixture of an ionizable cationic lipid, phospholipid, cholesterol and PEG-lipid, and the TCV-containing composition is organic-solvent and/or detergent free.

The organic solvent-free, detergent-free TCVs as discussed herein can be used for treatment of appropriate diseases and conditions, for example via gene therapy. The organic solvent-free, detergent-free TCVs as discussed herein improve the delivery of RNA, DNA, and RNP gene therapy products to human patients. The organic solvent-free, detergent-free TCVs effectively deliver gene therapy (including but not limited to mRNA, siRNA, and RNP) products to brain cells or other target cells. The underlying cause of many human disorders is the loss-of-function of a required protein or the toxic gain-of-function of a mutant protein. These causes are treatable, and even reversible, using the organic solvent-free, detergent-free TCVs herein.

Some examples of such treatment include gene therapy in the central nervous system for treating neurological disorders (some cases of Alzheimer's disease, Parkinson's disease, Huntington's disease, frontotemporal dementia, amyotrophic lateral sclerosis, spinal muscular atrophy, etc.).

The organic solvent-free, detergent-free TCVs as discussed herein can also genetically "knockdown" the mutant genes/gene products, for example via targeted, safe delivery of siRNA or RNP, gene replacement therapy with mRNA, or correction of the causal, native DNA mutation with RNP-mediated gene editing. Two specific examples of human diseases that can be targeted in this manner are Huntington's disease (HD) and frontotemporal dementia (FTD).

Huntington's disease is a progressive, incurable, neurodegenerative disease with a dominant pattern of inheritance. An expanded CAG nucleotide repeat sequence in the huntingtin (HTT) gene is responsible for the disease. The huntingtin protein (HTT) encoded by the mutant HTT gene contains an expanded polyglutamine repeat that confers a toxic gain-of-function to the gene product. Lowering the brain levels of mutant huntingtin protein is the principal therapeutic strategy currently being pursued to slow or stop disease progression in HD, and can be effected and improved using the organic solvent-free, detergent-free TCVs as discussed herein. TCVs loaded with siRNA targeting HTT expression or with RNP selected cargos designed to decrease huntingtin expression or toxicity will be effective therapies for HD. Frontotemporal dementia has many causes, but loss of the protein progranulin (a potential brain survival factor) is one well-described cause. The organic solvent-free, detergent-free TCVs as discussed herein can deliver progranulin mRNA or RNPs designed to either express progranulin or correct the underlying DNA mutation causing progranulin loss (respectively) will increase brain levels of progranulin and will be effective therapies for FTD. Increasing progranulin with TCVs expressing progranulin mRNA can also be a neuroprotective strategy for many common neurological diseases such as Alzheimer's disease, Parkinson's disease, and amyotrophic lateral sclerosis.

EXAMPLES OF MATERIALS AND METHODS

Materials 1,2-Dioleyloxy-3-dimethylamino-propane (DODMA) was purchased from Cayman Chemical (Ann Arbor, MI). 1,2-dioleoyl-3-dimethylammonium-propane (DODAP), 1,2-dioleoyl-sn-glycero-3-phosphocholine (DOPC), 1,2-dioleoyl-sn-glycero-3-phosphoethanolamine (DOPE), and 1,2-distearoyl-sn-glycero-3-phosphocholine (DSPC) were purchased from Avanti Polar Lipids (Alabaster, AL). Cholesterol was purchased from Sigma Aldrich (St. Louis, MO). PEG-DMG was synthesized previously described (Akinc, Zumbuehl et al. 2008). All lipids were maintained as ethanol stocks. siRNA targeting firefly luciferase (siLuc) (Basha, Ordobadi et al. 2016) was purchased from Integrated DNA Technologies (Coralville, IA). siRNA against murine hdh was purchased from Ambion (Silencer® Select Pre-designed siRNA, Invitrogen, Carlsbad, CA).

Preparation of Transfection Competent Vesicles (TCVs)

Lipid components (ionizable cationic lipids, phospholipids, cholesterol and PEG-lipid) were dissolved in ethanol at appropriate ratios to achieve a final concentration of 20-35 mM total lipid. An aqueous phase was prepared containing 25 mM sodium acetate pH 4 buffer. The two solutions were combined using two established nanoparticle preparation techniques: rapid-mixing and extrusion.

Rapid-Mixing:

The organic phase containing lipids was mixed with the aqueous phase through a T-junction mixer fabricated to meet the specifications of the PEEK Low Pressure Tee Assembly (1/16", 0.02 in thru hole, Part #P-712) at a final flow rate of 20 ml/min with a 1:3 organic: aqueous (v/v) ratio (Jeffs, Palmer et al. 2005; Kulkarni, Tam et al. 2017; Kulkarni, Darjuan et al. 2018). The resulting suspension was dialyzed against 1000-fold volume of 25 mM sodium acetate pH 4 buffer to remove ethanol.

Extrusion:

Lipids were dissolved in ethanol to a final concentration of 35 mM. Particles were generated by rapidly adding 25 mM sodium acetate pH 4 was to the ethanolic solution to achieve a final concentration of 30% ethanol (v/v) as described elsewhere (Maurer, Wong et al. 2001). The resulting nanoparticle suspension was extruded three times through 2×80 nm polycarbonate membranes at ambient temperature. Following extrusion, the particles were buffer-exchanged to remove ethanol.

Analysis of Transfection Competent Vesicles (TCVs)

Lipid concentrations were determined by assaying for the cholesterol content using a T-Cholesterol Assay Kit (Wako Chemicals, Mountain View, CA) and extrapolating total lipid concentration as described elsewhere (Chen, Tam et al. 2014). Nucleic acid entrapment was determined using the RiboGreen Assay as previously described (Chen, Tam et al. 2014; Leung, Tam et al. 2015).

Cryogenic Transmission Electron Microscopy

Cryo-TEM was performed as described previously (Kulkarni, Darjuan et al. 2018). Briefly, TCVs were concentrated to a total lipid concentration of approximately 20 mg/mL using an Amicon centrifugal concentration unit (10 kDa NWCO). A small volume (3-5 uL) of material was applied to a glow-discharged copper grid and plunge-frozen using an FEI Mark IV Vitrobot (Hillsboro, OR). The grids were stored under liquid nitrogen until imaged. All imaging was performed using an FEI Tecnai G2 instrument operating at 200 kV in low-dose mode. Images were captured using an FEI Eagle 4 k CCD bottom-mount detector. All sample preparation and imaging was performed at the UBC BioImaging Facility (Vancouver, BC).

Cell Culture and Reagents:

All base cell culture media and B27 neuronal supplement were purchased from Gibco (Thermo Fisher, Waltham, MA). Hank's balanced salt solution (HBSS), penicillin-streptomycin, L-glutamine, and trypsin solutions were obtained from Hyclone (Logan, UT). HEK293 cells were plated on clear-bottom, white-walled plates from Corning (Corning, NY). Primary cortical cells were plated onto tissue culture-treated plates (Fisher), coated with poly-D-lysine (Sigma, St. Louis, MO). Hygromycin B was obtained from Invitrogen (Carlsbad, CA). Recombinant ApoE4 was acquired from Peprotech (Rocky Hill, NJ).

To measure cell viability and luciferase levels in HEK293 cells, the ONE-Glo+Tox kit from Promega (Madison, WI) was used. Cell viability in primary neurons was measured via MTT in vitro toxicology kit from Sigma (St. Louis, MO).

Luciferase Reporter HEK293 Cells:

Generation of the HEK293 cell line with a stably-integrated luciferase reporter construct (HEK-Luc cells) has been described previously (De Souza, Islam et al. 2016). Cells were maintained at 37° C. in a humidified atmosphere of 95% air, 5% $CO_2$ in DMEM high glucose, supplemented with 10% fetal bovine serum, 2 mM L-glutamine and 125 μg/mL hygromycin B. Cells were plated at a density of 12,000-20,000 cells/well in a white-walled 96-well plate.

Primary Cell Culture:

Cortical cultures were prepared from embryonic day E17.5 C57BL/6J and FVB.YAC128 mice. Briefly, cortices were dissected in ice cold HBSS, and the tissue was digested using a 0.05% trypsin (Hyclone) solution for 10 minutes at 37° C. The cortices were then triturated through a 5 mL pipette 5 times, and an additional 5-7 times with a 200 μL pipette tip added. Cells were pelleted by centrifugation for 5 minutes at 800 rpm, washed with HBSS, and then re-suspended in warm neurobasal media supplemented with B27, 2 mM L-glutamine (Hyclone) and 1% penicillin/streptomycin (Hyclone). Cortical neuronal cultures were plated onto poly-D lysine-coated 24-well plates at a density of $1.5\times10^5$ cells/well. Cells were maintained at 37° C. in a humidified atmosphere of 95% air, 5% $CO_2$.

Transfection:

All reagents were mixed on the bench-top. Empty TCVs containing 50% cationic lipid were mixed with siRNA at a ratio of 0.058 mg siRNA per μmole lipid. TCVs containing 20% cationic lipid were mixed at 0.022 mg siRNA per μmole lipid. TCV suspension was mixed with siRNA briefly by pipette and incubated at room temperature for 10 minutes.

HEK293 cells were plated 24 hours before transfection. Complete DMEM media was added to the TCV: siRNA mixture for a final concentration of 3.3 μg/mL siRNA, and a complete change of media was performed at the time of transfection.

Primary neuronal cells were grown in vitro for 7 days before transfection. Complete neurobasal media with 2-6 μg/mL of recombinant ApoE4 was added to the TCV: siRNA suspension, and half the media was replaced from each well.

Luciferase Assay:

Forty-eight to seventy-two hours post-transfection, HEK293 cells were assayed for cell viability and luminescence using the ONE-Glo+Tox kit (Promega) according to the manufacturer's instructions. Briefly, live cell reagent was added to each well, and cells were incubated for 30 minutes at 37° C. The plate was assayed on a plate reader (POLARstar Omega plate reader, BMG LABTECH) at an excitation of 400 nm, and read at an emission wavelength of 510 nm. ONE-Glo reagent was then added, and the plate incubated at room temperature for 3 minutes. Luminescence was measured via light output through the lens of the same plate reader. Values are presented as % control and represent N=4 wells per condition.

MTT Assay:

Primary cortical neurons were assayed for cell viability via MTT assay 72 hours after transfection in a 24-well plate. MTT reagent (3-(4,5-dimethylthiazol-2-yl)-2,5-diphenyltetrazolium bromide, or MTT) was reconstituted in HBSS to a final concentration of 5 mg/mL, and added to each well at 10% v/v. Cells were incubated at 37° for 4 hours. The media was removed, and 250 μL solubilization solution was added to each well. Absorbance was measured at 570 nm. Values are presented as % control and represent N=3 wells per condition.

Quantitative RT-PCR

Adherent primary cortical cells were washed once in sterile PBS prior to being scraped off the plate in 600 μL lysis buffer containing 1% 2-mercaptoethanol and immediately frozen at −80° C. Total RNA was subsequently extracted using the PureLink RNA mini kit (Invitrogen) performed according to the manufacturer's instructions. Reverse transcription of all samples was carried out using the Superscript VILO kit (Invitrogen) according to the manufacturer's instructions, using 250 ηg of total RNA as input for cDNA synthesis and 5 ηg diluted RNA for the quantitative PCR reaction. Quantification of hdh mRNA levels was accomplished using the standard curve method, with amplification of target mRNA and control genes in separate wells, performed using FastSybr (Applied Biosystems) and conducted on a Step-One ABI System (Applied Biosystems). Each sample was run in duplicate. The relative amount of mRNA in each well was calculated as the ratio between hdh mRNA and a control gene, Csnk2a2. Values are presented as % control and represent N=3 wells per condition.

Ribonucleoprotein (RNP) Complex Materials and Formation

All materials for RNP formulation, including guide RNAs (gRNAs), tracrRNA, single-stranded oligodeoxynucleotides (ssODN), and recombinant Cas9 protein, were obtained from IDT (San Jose, CA). The gRNA sequence used to target luciferase was provided by IDT (San Jose, CA). The gRNA sequence targeting human progranulin (GRN) binds to exon 5 of the gene. The ssODN sequence used for homology-directed repair (HDR) was engineered to introduce a 4 bp deletion into exon 5 of GRN.

RNP assembly was performed according to the manufacturer's specifications. Briefly, the guide RNA (gRNA) complex was formed by incubating equimolar ratios of crRNA: tracrRNA. such as 1 μM tracrRNA with 1 μM gRNA, at 95° C. for 5 minutes. The mixture was then allowed to cool at room temperature for 20-30 minutes. RNPs were subsequently formed by combining gRNA duplexes with Cas9 protein at equimolar ratios and allowing the mixture to stand at room temperature for 5 minutes prior to use.

Transfection of Mammalian Cells with Nucleic Acid:

Empty organic solvent-free, detergent-free TCVs as discussed herein, as well as commercially available reagents for comparison, were mixed with selected cargo on the benchtop. TCVs were mixed with nucleic acid selected cargo at a range of ratios of 0.01-0.2 mg nucleic acid per μmole lipid. TCV suspension was mixed with siRNA briefly by pipette and incubated at room temperature for 10 minutes.

HEK293 cells were plated 24 hours before transfection. Complete DMEM media was added to the TCV:nucleic acid mixture for a final concentration of 0.33-3.3 μg/mL siRNA, or 0.1-1 μg/mL mRNA a complete change of media was performed at the time of transfection. Primary neuronal cells were grown in vitro for 7 days before transfection. Complete neurobasal media with 2-6 μg/mL of recombinant ApoE4 was added to the TCV:nucleic acid suspension, and half the media was replaced from each well.

Cells were treated with Mirus TransIT-TKO per manufacturer's instructions. Briefly, Mirus TransIT-TKO was added to serum-free media at a concentration of 5 μL Mirus/100 μL serum-free media. siRNA was then added to the tube, pipetted gently to mix, and incubated at room temperature for 15-30 minutes. The solution was then transferred onto cells, and the final concentration of Mirus was 5 μL/1 mL of complete media. The final concentration of siRNA was 25 nM.

Transfection of Mammalian Cells with RNPs:

0.5-20 mM TCV and 0.5-20 μM RNP were combined at a 467-5000 molar ratio and allowed to incubate at room temperature for 10 minutes. Separately, 1-10 μM solution of ssODN was combined with TCV and this mixture was incubated at room temperature for 5-15 minutes. In some instances, an equimolar amount of ssODN was added to the RNP complex solution prior to the addition of TCVs.

TCVs containing RNPs and ssODN mixtures were combined, and complete media was added to a final concentration of 10-200 nM of RNPs and ssODN each. A full media change was performed on HEK cells, which were plated 24 hours prior. Primary neuronal cells were grown in vitro for 5-7 days before transfection. Complete neurobasal media with 2-6 μg/mL of recombinant ApoE4 was added to the TCV:RNP mixture, and half the media was replaced from each well.

Cells were treated with Lipofectamine RNAiMAX reagent per manufacturer's instructions. Briefly, RNP complexes were prepared and added to a mixture of serum-free media and RNAiMAX. incubated at room temperature for 5 minutes, and added onto plated cells.

PCR for Detection of Homology-Directed Repair

Polymerase chain reaction (PCR) was used to amplify GRN exon 5 from genomic DNA extracted from transfected HEK293 cultures using forward primers specific for either the wild-type (WT) or mutant GRN alleles and a common reverse primer. PCR was performed using MyTaq (Bioline, USA) according to the manufacturer's instructions. PCR products were separated by gel electrophoresis on a 1.5% agarose gel stained with SybrSafe and imaged under UV light.

Immunocytochemistry

Cells were fixed for 15 minutes using a solution of 3-4% paraformaldehyde. The cells were permeabilized for 15 minutes in PBS containing 0.1% Triton-X (PBST). Cells were incubated overnight at 4° C. with PBST containing a 1:1000 mixture of anti-Cas9 (Invitrogen) antibody. Cells were washed thrice with PBS and incubated with 1:1000 mixture of each Alexa Fluor 594 fluorescent secondary antibody (Invitrogen) and Phalloidin-iFluor 488 CytoPainter antibody (Abcam) for 1 hour at room temperature, washed again and incubated for 5 minutes with a solution containing DAPI to visualize nuclei.

Statistics

All statistical comparisons were performed as a one-way analysis of variance (ANOVA) with Bonferroni post-hoc analysis to compare individual means to control-treated cells and correct for multiple comparisons (Prism 6, Graphpad Software Inc.). A Student's t-test was used to compare individual means in the case of only two groups. A p-value less than 0.05 was considered significant.

RESULTS-RELATED EXAMPLES

Example 1: Empty Transfection-Competent Vesicles (TCVs) Entrap Nucleic Acid Efficiently without Organic Solvents Empty TCVs formulation produced by T-junction or SHM mixing exhibited entrapment efficiencies on the order of 85% or greater. We first tested the ability of TCVs composed of ionizable cationic lipids that span the range of observed in vivo gene silencing potencies (DODMA>>DLinDAP>DODAP) ("DLinDAP" is 1,2-dilineoyl-3-dimethylammonium-propane) to entrap nucleic acid without the aid of organic solvents or detergent.

Remarkably, in the absence of either, formulations composed of ionizable lipid/DSPC/Chol/PEG-lipid (50/10/39/1 mol %) achieve near complete entrapment of siRNA (>85%) when mixed at pH 4 at a ratio of 0.058 mg siRNA/μmol lipid followed by neutralisation with PBS (Table 1). The assay to determine entrapment is based on the exclusion of an RNA-binding dye from the nucleic acid by the lipid components. Thus, entrapment is considered the sequestration of RNA from the external medium in more than a transient manner (i.e., stable entrapment). Despite the lack of organic solvents or detergents in the production processes, the obtained TCV formulations surprisingly displayed entrapment efficiencies similar to those reported elsewhere for LNP-siRNA generated by rapid-mixing techniques using organic solvents (Belliveau, Huft et al. 2012; Chen, Tam et al. 2014; Leung, Tam et al. 2015; Chen, Tam et al. 2016).

TABLE 1

Entrapment efficiencies of nucleic acids for different formulations of TCVs.

| Name | Lipid formulation | Formulation process | Entrapment efficiency, % (mean ± SEM) |
|---|---|---|---|
| DODMA-50% | DODMA/DSPC/Chol/PEG (50/10/39/1) | T-junction mixing | 87.90 ± 3.94 |
| DLinDAP-50% | DLinDAP/DSPC/Chol/PEG (50/10/39/1) | T-junction mixing | 74.44 ± 7.18 |
| DODAP-50% | DODAP/DSPC/Chol/PEG (50/10/39/1) | T-junction mixing | 71.84 ± 5.76 |

Figure 13:
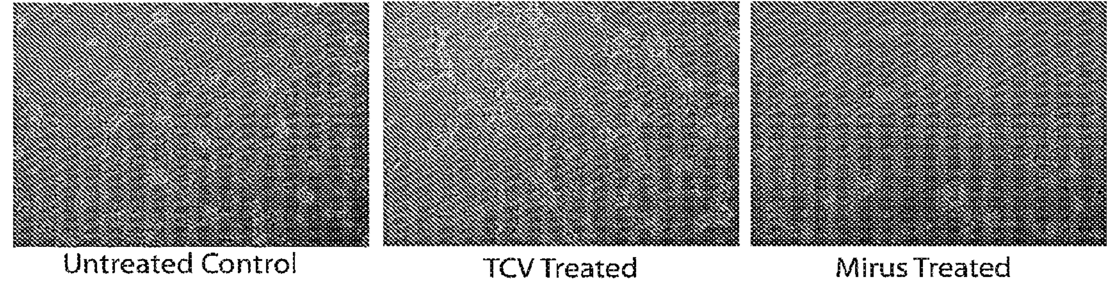
FIG. 13. Photomicrographs demonstrating cell viability for bench-top loading of siRNA into empty organic solvent-free, detergent-free TCVs in primary neurons. siRNA were delivered via organic solvent-free, detergent-free TCV (DODMA/DOPE/DSPC/Chol/PEG-lipid (20/30/10/39/1)) or using the commercially available Mirus TKO system (Mirus Bio) into primary neurons for cytotoxicity assessment. The siRNA delivered by bench-top loading into empty organic solvent-free, detergent-free TCV was significantly less toxic compared to the Mirus TKO system, as shown by photomicrographs.

Example 2: siRNA in Organic Solvent-Free, Detergent-Free Empty TCVs Displays Robust Knockdown in Immortalized Cells and Primary Neurons The ability to both entrap nucleic acid and subsequently deliver it in a non-toxic manner represent two separate hurdles. Upon determining that the non-organic solvent/non-detergent lipid-based TCVs discussed above efficiently entrapped nucleic acids, their ability to silence genes and their effect on cell viability was tested in two scenarios, as shown in FIGS. 1A-1D. First, the empty organic solvent-free, detergent-free TCVs were combined using bench-top loading with siLuc and used to treat HEK-Luc cells. Surprisingly, DODMA-based TCVs shows about 50% knockdown and performed better than DLinDAP and DODAP, which showed no indication of knockdown (FIG. 1A). None of the formulations displayed toxicity as measured by cell viability compared to untreated cells (FIG. 1B). Second, the efficacy and toxicity of the TCVs delivering siRNA was tested against the hdh gene in primary mouse cortical neurons. Once again (FIG. 1C), DODMA-TCVs displayed an about 50% gene knockdown efficacy, while DLinDAP-TCVs displayed less knockdown, and DODAP-TCVs displayed no difference from untreated cells. It should be noted that primary neurons are quite susceptible to the toxic effects of harmful transfection reagents such as those currently available commercially. FIG. 13 highlights the differences in the effect on viability.

Figure 2:
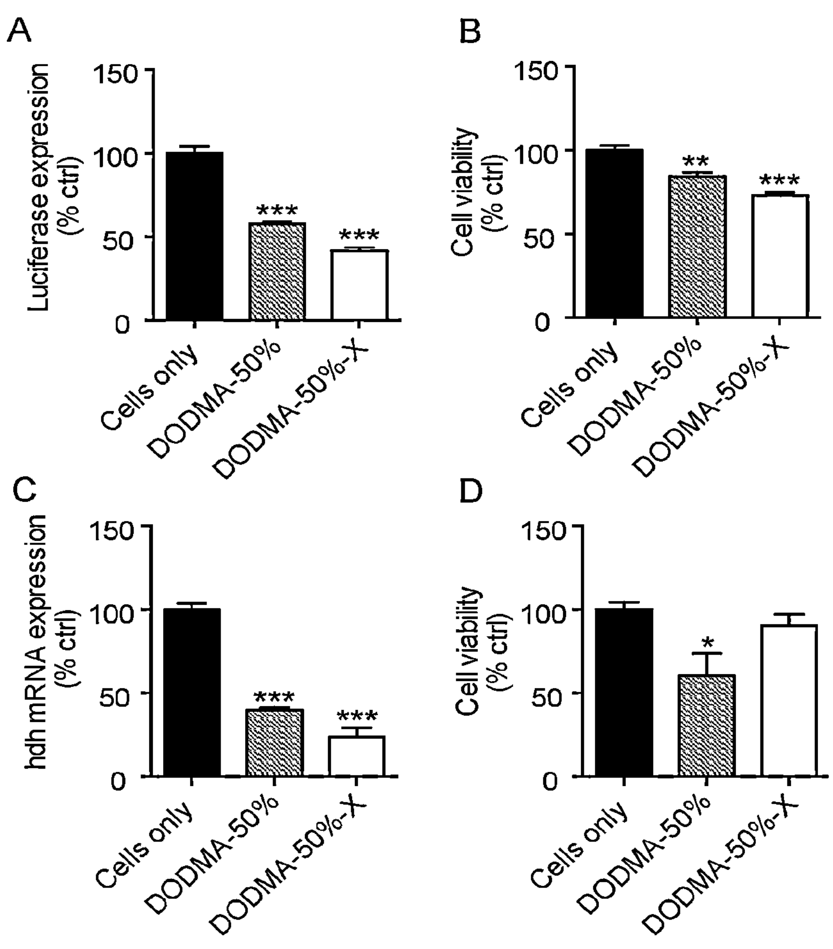
FIG. 2A-2D. The potency of organic solvent-free, detergent-free TCVs does not depend on the method of mixing used to generate the empty TCVs. (A) Relative luciferase expression in HEK-Luc cells after transfection with TCVs composed of 50% ionizable lipid and formed by either T-junction mixing (DODMA-50%) or extrusion (DODMA-50%-X). (B) Cell viability from the same set of transfections presented in (A) as % of control (cells only) wells. (C) Relative expression of hdh mRNA in primary cortical neurons after organic solvent-free, detergent-free TCV-mediated transfection of an siRNA targeting hdh using the same panel of TCVs presented in 2(A). (D) Cell viability as measured by MTT reduction for an equivalent set of transfections into primary cortical neurons using organic solvent-free, detergent-free TCVs to deliver an off-target (luciferase) siRNA. N=4 per condition for HEK-Luc cells, N=3 wells per condition for primary neurons. Data represent the mean±SEM. *p<0.05, p<0.01, *p<0.001 by Bonforroni post-hoc analysis after a one-way ANOVA with each condition compared to the control (cells only) condition.

Example 3: Multiple Mixing Processes can Produce Potent Organic Solvent-Free, Detergent-Free Empty TCVs In an effort to determine the role of the mixing aspect of the manufacturing process and the resulting particle size to achieve the potency shown in FIG. 1, organic solvent-free, detergent-free lipid-based empty TCVs containing ionizable lipids such as DODMA were produced through both T-junction mixing and extrusion. As shown in FIG. 2A, following bench-top loading of siRNA into empty TCVs there was significant knockdown of luciferase in HEK-Luc cells using both processes. There was no significant difference in the viability of cells treated with particles produced by T-junction or extrusion (FIG. 2B). Next, primary cortical neurons were treated with the same solvent-free, detergent-free lipid-based TCV formulations and it was determined that both processes result in particles with similar potency (FIG. 2C) and similar cell viability (FIG. 2D). In contrast, the toxicity of current transfection methods (FIG. 13) in primary cultures detracts from the goal of a non-toxic yet potent formulation.

Example 4: Organic Solvent-Free, Detergent-Free Empty TCVs Containing a Reduced Amount of Ionizable Lipid Facilitate Potent siRNA Delivery with Decreased Toxicity An established lipid composition, currently used in clinical formulations (see Patisiran), includes a significant amount of ionizable cationic lipid (50 mol %) (Jayaraman, Ansell et al. 2012; Suhr, Coelho et al. 2015). While such high amounts allow for improvements in the effective dose to achieve 50% gene silencing ($ED_{50}$) in vivo (Jayaraman, Ansell et al. 2012), the persistence of lipid metabolites following administration (Maier, Jayaraman et al. 2013; Sabnis, Kumarasinghe et al. 2018) and the toxicity associated with those molecules renders the formulation toxic in high-dose regimens and repeat administration (or to sensitive cell types). The current compositions, TCVs, etc., can be comprised of materials that are biodegradable or facilitate elimination. Here, the current compositions, TCVs, etc., decrease the amount of toxic ingredients maintaining transfection potency.

Figure 3:
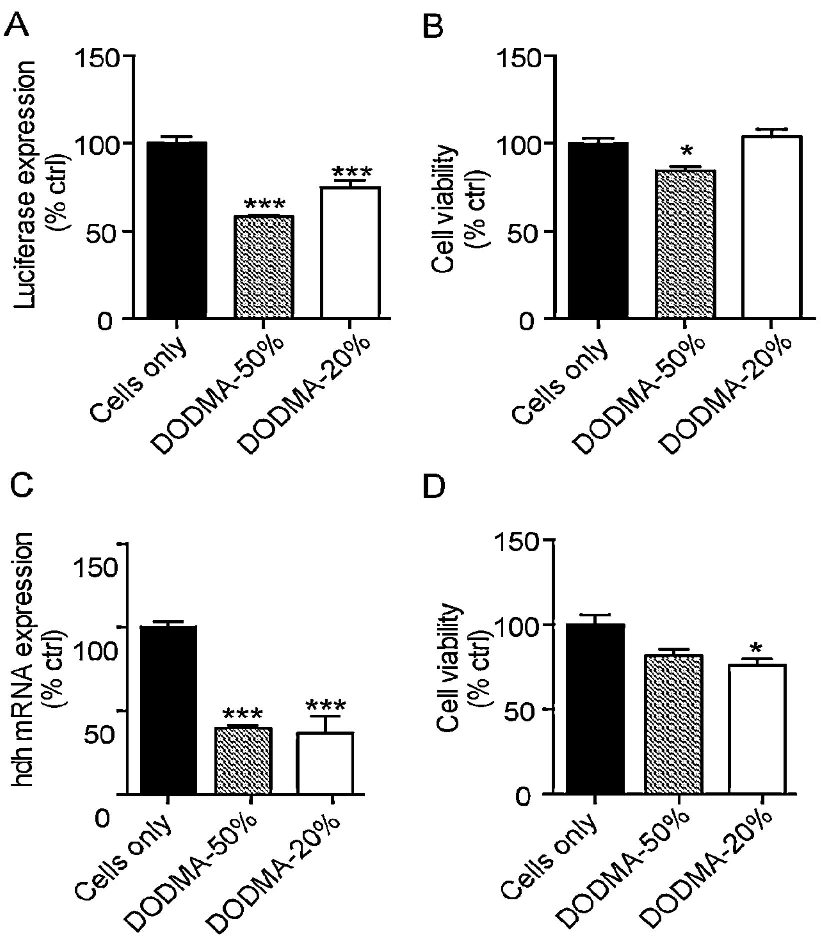
FIG. 3A-3D. Organic solvent-free, detergent-free empty TCVs containing a reduced amount of ionizable lipid facilitate potent siRNA delivery with decreased toxicity. (A) Relative luciferase expression in HEK-Luc cells after transfection with TCVs composed of either 20% or 50% of the ionizable lipid 1,2-Dioleyloxy-3-dimethylamino-propane (DODMA). (B) Cell viability from the same set of transfections presented in (A) as % of control (cells only) wells. (C) Relative expression of hdh mRNA in primary cortical neurons after organic solvent-free, detergent-free TCV-mediated transfection of an siRNA targeting hdh using the same panel of TCVs presented in 3(A). (D) Cell viability as measured by MTT reduction for an equivalent set of transfections in primary cortical neurons using organic solvent-free, detergent-free TCVs to deliver an off-target (luciferase) siRNA. N=4 per condition for HEK-Luc cells, N=3 wells per condition for primary neurons. Data represent the mean±SEM. *p<0.05, p<0.01, *p<0.001 by Bonforroni post-hoc analysis after a one-way ANOVA with each condition compared to the control (cells only) condition.

The transfection competency of a formulation composed of DODMA/DOPE/DSPC/Chol/PEG-lipid (20/30/10/39/1 mol % respectively) to silence luciferase in HEK-Luc cells was tested. A 40% knockdown of luciferase expression was observed (FIG. 3A) with no significant toxicity (FIG. 3B). Next, we tested the ability of TCVs with 20 mol % of ionizable lipid to deliver siRNA to primary neurons as compared to DODMA-TCVs at 50 mol %. All formulations displayed ~60% knockdown of hdh (FIG. 3C), while a DODMA formulation produced via T junction mixing showed significantly improved cell viability (FIG. 3C).

Figures 4A, 4B:
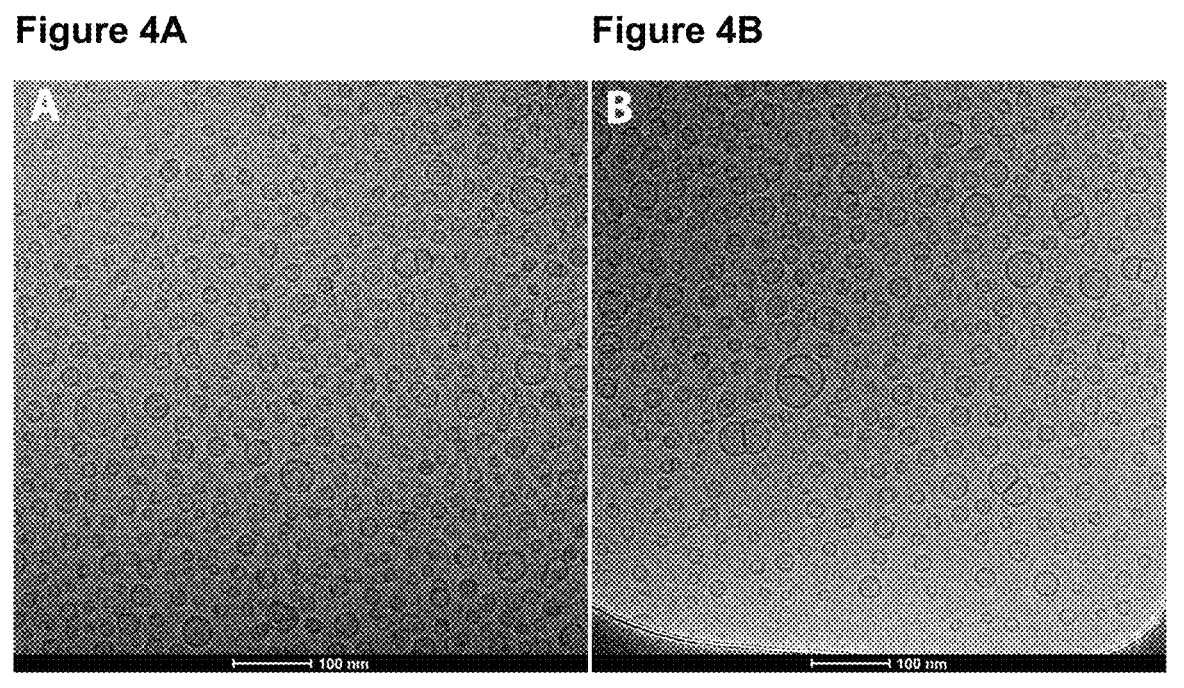

Example 5: Incorporation of DOPE Does Not Change Organic Solvent-Free, Detergent-Free Empty TCV Morphology Improving the potential for Hu phase formation in a nucleic acid delivery vehicle can be an important factor to facilitate membrane fusion in the endosome (Hafez, Maurer et al. 2001). In the present approach, two exemplary lipids able to adopt Hu phases are DOPE (in isolation) and DODMA (when protonated and combined with anionic lipids). To determine if the incorporation of DOPE in organic solvent-free, detergent-free TCVs resulted in premature Hu phase formation, cryo-TEM was performed on DODMA-TCVs at 20 mol % and the equivalent formulation composed of 50 mol % DODMA. The resulting structures (FIGS. 4A, 4B) are visualized as bilayer structures with no indication of Hu phase.

Previous work by others has suggested the presence of $H_{II}$-like internal structures within the core LNP formulations regardless of siRNA content (Leung, Hafez et al. 2012; Leung, Tam et al. 2015). It has since been shown that LNP-siRNA do not contain such structures, but rather have siRNA immobilised between closely apposed layers of lipid (Kulkarni, Darjuan et al. 2018) giving the overall particle a multi-lamellar or onion-like morphology. In the absence of siRNA, LNP formulations adopt an electron-dense core containing an oil-phase lipid. Thus, the examples herein demonstrate that TCV morphology is drastically different from LNP systems but still have highly efficient transfection potency.

Example 6: Organic Solvent-Free, Detergent-Free Empty TCVs Can Be Used to Deliver Functional Ribonucleoproteins (RNPs)

Figure 5:
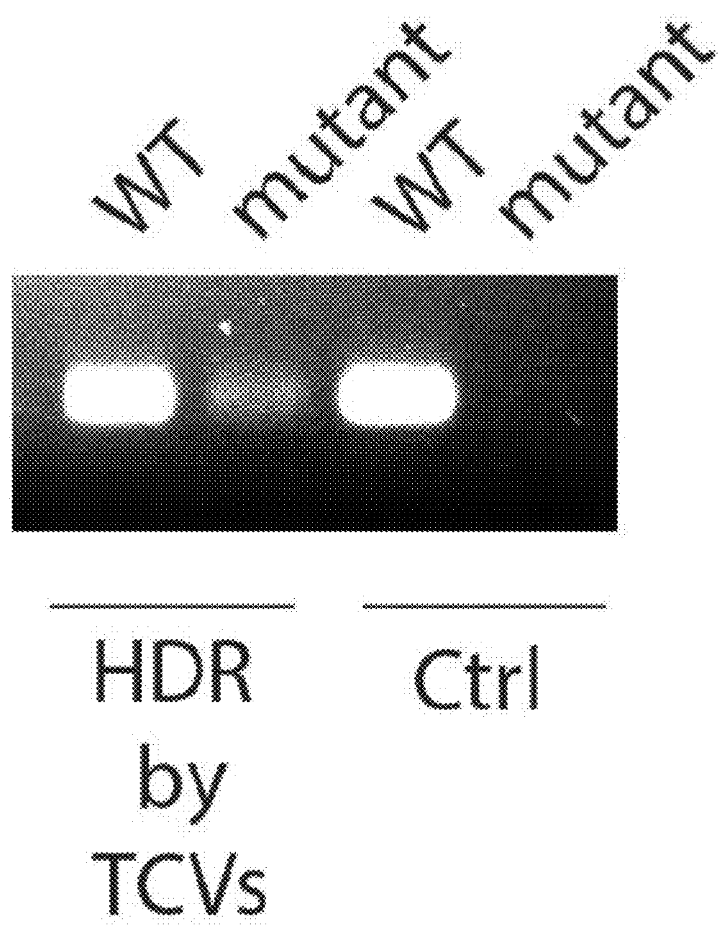
FIG. 5. Organic solvent-free, detergent-free empty TCVs herein can be used to deliver functional ribonucleoproteins (RNPs). HEK293 cells were transfected with Cas9 RNPs and a single-stranded oligodeoxynucleotide (ssODN) repair template, both delivered by organic solvent-free, detergent-free TCVs produced according to the methods herein. The Cas9 protein was complexed to a guide targeting the GRN gene. DNA was extracted from the cells 48 hrs post-transfection. PCR was used to specifically detect the wild-type (WT) GRN allele or a mutant GRN allele, which is only present when homology-directed repair (HDR) incorporates the delivered ssODN into a DNA double-stranded break produced by Cas9. The mutant GRN allele can be detected after TCV-mediated delivery of the Cas9 RMP but is not present in control (Ctrl) cells.

As shown in FIG. 5, organic solvent-free, detergent-free empty TCVs herein were also tested for their ability to deliver a protein selected cargo complexed with nucleic acid into a mammalian cell. Briefly, a ribonucleoprotein complex consisting of recombinant Cas9 protein and a guide RNA targeting exon 5 of the progranulin gene was assembled and combined with empty TCVs via bench-top loading (DODMA/DOPE/DSPC/Chol/(20/30/10/40 mol % respectively) at a molar ratio of 467:1 (TCV:RNP complex). Separately, a single stranded oligodeoxynucleotide designed to introduce a 4 bp deletion into exon 5 of the progranulin gene was combined with TCVs at a molar ratio of 4275:1 (TCV:nucleic acid). The two preparations of TCVs containing their respective selected cargoes were combined to achieve a final concentration of 10 nM RNPs and 10 nM ssODN, and then added to HEK cells. After 48 hours, PCR was employed to determine whether homology-directed repair had occurred at the progranulin gene target using forward primers specific for either the wild type or mutant allele. As shown in FIG. 5, cells exposed to the combination of TCVs containing each of ribonucleoprotein complexes and the ssODN resulted in the insertion of the 4 bp deletion via homology-directed repair (second lane of FIG. 5, labelled mutant), whereas untreated control cells did not result in any genetic alternation at the exon 5 site of the progranulin gene (third and fourth lanes of FIG. 5).

Example 7: Further Examples of Organic Solvent-Free, Detergent-Free Empty TCVs Used to Deliver Functional Ribonucleoproteins (RNPs)

Organic solvent-free, detergent-free empty TCVs were used to deliver functional ribonucleoproteins (RNPs) using methods as discussed above.

Figure 6:
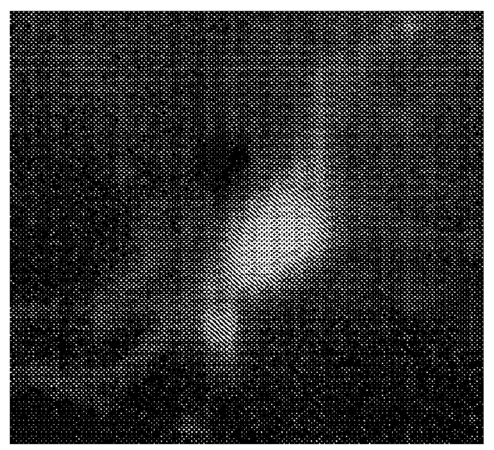
FIG. 6. Photomicrographs of Cas9 located within a primary neuron. RNP delivered via organic solvent-free, detergent-free TCV as discussed herein can be detected using a fluorescent antibody against the Cas9 protein, displayed in red. The untreated control has no such red fluorescent signals. Blue signal=nucleic acid (DAPI stain), green signal=phalloidin (F-actin stain).
Figure 6:
Figure 6:
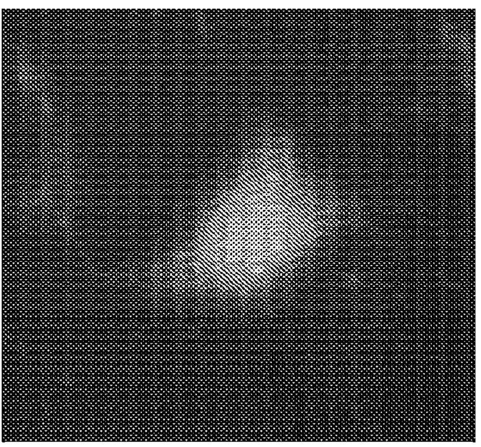

FIG. 6 provides a photomicrograph of Cas9 located within a primary neuron. RNP delivered via organic solvent-free, detergent-free TCV as discussed herein can be seen within a primary neuron as fluorescent signals; the untreated control has no such fluorescent signals. More specifically, immunocytochemistry of primary neuronal cells showed localization of Cas9 protein (red) within the nucleus (blue) of cortical neurons derived from mice. Cells were also stained for phalloidin (green) to show cellular morphology.

Figure 7:
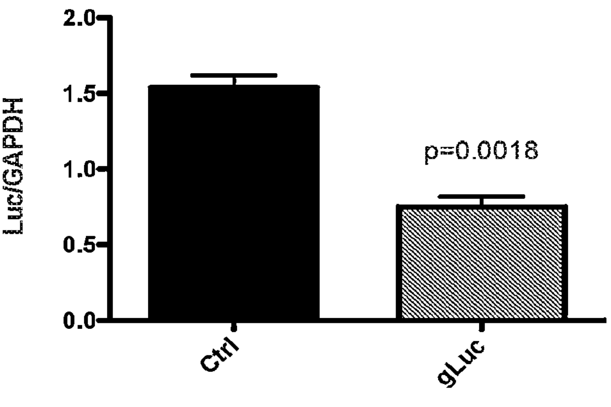
FIG. 7. Graph demonstrating transcriptional knockdown by RNP delivered via bench-top loading of RNP into empty organic solvent-free, detergent-free TCV in HEK cells. HEK293 cells were transfected with Cas9 RNPs targeting luciferase. TCVs of formula (DODMA/DOPE/DSPC/Chol (20/30/10/40)) were loaded at the bench. Relative levels of luciferase mRNA in HEK cells show significant knockdown compared to control ("ctrl" in the graph) when measured by qPCR. N=3 per group. Data represent the mean±SEM. p=0.0018 by Student's t-test.
Figure 8:
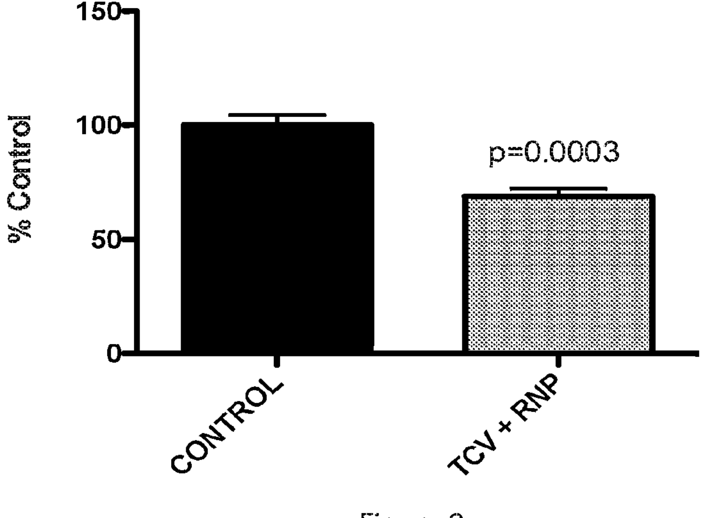
FIG. 8. Graph demonstrating protein knockdown by RNP delivered via bench-top loading of RNP into empty organic solvent-free, detergent-free TCV in HEK cells. HEK293 cells were transfected with Cas9 RNPs targeting luciferase. TCVs of formula (DODMA/DOPE/DSPC/Chol (20/30/10/40)) were loaded at the bench. Relative levels of luciferase protein in HEK cells show significant knockdown compared to control ("ctrl" in the graph) when measured by ONE-Glo. N=3 per group. Data represent the mean±SEM. p=0.0003 by Student's t-test.

FIG. 7 provides a graph demonstrating gene knockdown by RNP delivered via organic solvent-free, detergent-free TCV in HEK cells. RNP delivered via organic solvent-free, detergent-free TCV into HEK cells show significant knockdown of luciferase transcript compared to control ("ctrl" in the graph). FIG. 8 provides a graph demonstrating protein knockdown by RNP delivered via organic solvent-free, detergent-free TCV in HEK cells. RNP delivered via organic solvent-free, detergent-free TCV into HEK cells show significant knockdown of luciferase protein compared to control ("control" in the graph), p=0.0003.

Figure 9:
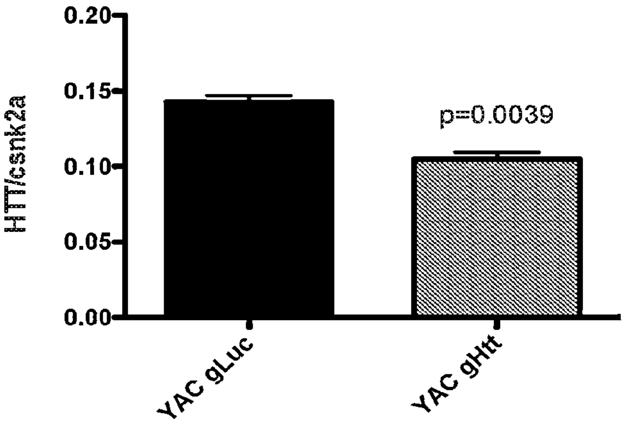
FIG. 9. Graph demonstrating transcriptional knockdown by RNP delivered via bench-top loading of RNP into empty organic solvent-free, detergent-free TCV in primary cortical neurons. Primary cortical neurons were transfected with Cas9 RNPs targeting Human Huntingtin (HTT). TCVs of formula (DODMA/DOPE/DSPC/Chol (20/30/10/40)) were loaded at the bench. Relative levels of HTT mRNA in primary neurons show significant knockdown compared to control ("gLuc" in the graph) when measured by qPCR. N=3 per group. Data represent the mean±SEM. p=0.0039 by Student's t-test.

FIG. 9 provides a graph demonstrating gene knockdown by RNP delivered via organic solvent-free, detergent-free TCV in primary neurons. RNP delivered via organic solvent-free, detergent-free TCV into primary cortical neurons show significant mRNA knockdown by quantitative real-time PCR (qRT-PCR) assay, p=0.0039.

Turning to some further discussion of these Figures, FIGS. 7 and 8 show that RNP delivered via bench-top loading of the empty TCV herein show robust knockdown of a reporter gene, luciferase, in HEK cells. This was demonstrated by measuring the luciferase output (functional protein) as well as mRNA levels of the luciferase mRNA via qRT-PCR. This same approach of RNP delivery was used to disrupt expression of the huntingtin gene in cortical neurons derived from FVB.YAC128 mice expressing the full-length human huntingtin gene carrying a disease mutation (FIG. 9). mRNA levels of huntingtin were quantified from primary cortical neurons using qRT-PCR after 72 hours of incubation with TCV:RNP mixture.

Example 8: Examples of mRNA Delivered via Organic Solvent-Free, Detergent-Free TCV Bench-top loading of organic solvent-free, detergent-free empty TCVs used to deliver mRNA using methods as discussed above.

Figure 10:
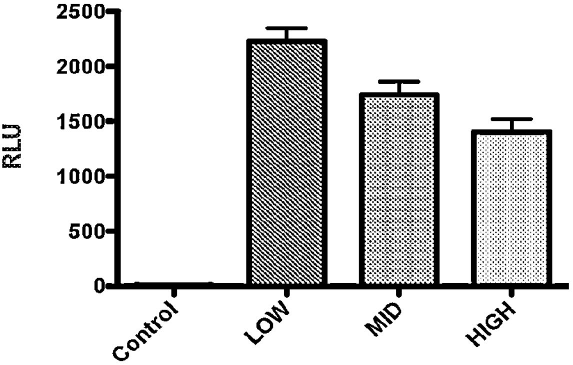
FIG. 10. Graph demonstrating mRNA expression for mRNA delivered via organic solvent-free, detergent-free TCV in HEK cells. Luciferase mRNA was delivered via organic solvent-free, detergent-free TCV (DODMA/DOPE/DSPC/Chol (20/30/10/40)) into HEK cells at different ratios Low=0.029 mg mRNA/μmol lipid, mid=0.058 mg mRNA/μmol lipid, high=0.116 mg mRNA/μmol lipid. All ratios demonstrated significant expression compared to the control, with the lowest ratio demonstrating the highest expression. mRNA expression measured by ONE-Glo+Tox kit (Promega), N=3 per condition.

FIG. 10 provides a graph demonstrating expression of mRNA delivered via organic solvent-free, detergent-free TCV in HEK cells. mRNA was delivered via organic solvent-free, detergent-free TCV (DODMA/DOPE/DSPC/Chol (20/30/10/40)) into HEK cells at different ratios, Low=0.029 mg mRNA/μmol lipid, mid=0.058 mg mRNA/μmol lipid, high=0.116 mg mRNA/μmol lipid. All ratios demonstrated significant expression compared to the control, with the lowest ratio demonstrating the highest expression.

Figure 11:
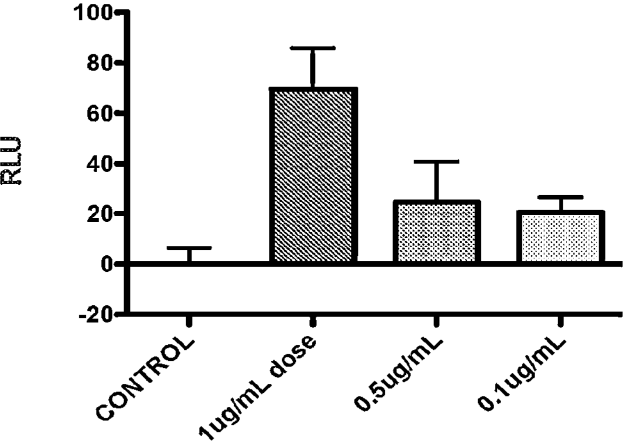
FIG. 11. Graph demonstrating mRNA expression for mRNA delivered via organic solvent-free, detergent-free TCV in primary cortex neurons. Luciferase mRNA was delivered via organic solvent-free, detergent-free TCV (DODMA/DOPE/DSPC/Chol (20/30/10/40)) into primary cortical neurons at different dosages. All dosages demonstrated significant expression compared to the control. mRNA expression measured by ONE-Glo+Tox kit (Promega), N=3 per condition.

FIG. 11 provides a graph demonstrating expression of mRNA delivered via bench-top loading of empty organic solvent-free, detergent-free TCV in primary cortical neurons. mRNA was delivered via organic solvent-free, detergent-free TCV (DODMA/DOPE/DSPC/Chol (20/30/10/40)) into primary cortical neurons at different dosages. All dosages demonstrated significant expression compared to the control.

Turning to some further discussion of these Figures, FIG. 10 demonstrates that bench-top loading of organic solvent-free, detergent-free empty TCVs as discussed herein can be used to deliver mRNA encoding for a functional protein into cells. Briefly, organic solvent-free, detergent-free TCVs were mixed gently using a pipette with mRNA encoding the firefly luciferase mRNA, in a range of ratios from 0.029-0.116 mg nucleic acid:1 μmole lipid. This mixture was incubated at room temperature for 5-20 minutes, before addition of complete culture media and then transferred into wells containing HEK cells (see FIG. 10) or primary cortical neurons (FIG. 11). Luciferase output was measured using the ONE-Glo luciferase assay kit from Promega, per manufacturer's instructions. The results demonstrate the production of luciferase protein within these cells types across a range of selected cargo:TCV concentrations and doses.

Example 9: Comparison of Organic Solvent-Free, Detergent-Free TCVs to Market-Available Products Bench-top loading of empty organic solvent-free, detergent-free TCVs was used to deliver siRNA or RNP to HEK cells or primary neurons using methods as discussed above, and then were contrasted to equivalent transfections using commercially available systems. The organic solvent-free, detergent-free TCVs herein outperformed the commercially available systems.

Figure 12:
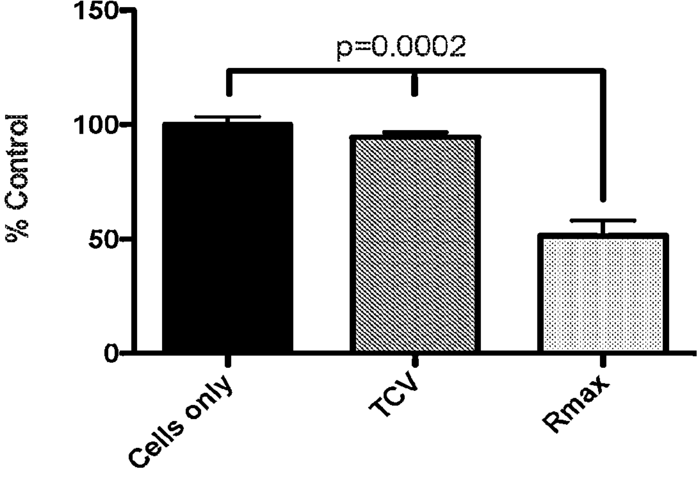
FIG. 12. Graph demonstrating cell viability for RNP in organic solvent-free, detergent-free TCVs in HEK cells. RNP were delivered via organic solvent-free, detergent-free TCV (DODMA/DOPE/DSPC/Chol (20/30/10/40)) or using RNAiMax ("Rmax" in the figure; ThermoFisher Scientific) into HEK cells for cytotoxicity assessment. The organic solvent-free, detergent-free TCV were significantly less toxic compared to RNAiMax, p=0.0002. Toxicity was assed using ONE-Glo+Tox kit (Promega), N=3 per group.

FIG. 12 provides a graph demonstrating cell viability for organic solvent-free, detergent-free TCVs in HEK cells. RNP were delivered via organic solvent-free, detergent-free TCV (DODMA/DOPE/DSPC/Chol (20/30/10/40)) or using RNAiMax ("Rmax" in the figure; ThermoFisher Scientific) into HEK cells for cytotoxicity assessment. The organic solvent-free, detergent-free TCV were significantly less toxic compared to RNAiMax, p=0.0002.

FIG. 13 provides photomicrographs demonstrating cell viability for bench-top loading of siRNA into empty organic solvent-free, detergent-free TCVs in primary neurons. siRNA were delivered via organic solvent-free, detergent-free TCV (DODMA/DOPE/DSPC/Chol/PEG-lipid (20/30/10/39/1)) or using the commercially available Mirus TKO system (Mirus Bio into primary neurons for cytotoxicity assessment. The organic solvent-free, detergent-free TCV were significantly less toxic compared to the Mirus TKO system, as shown by photomicrographs.

Figure 14:
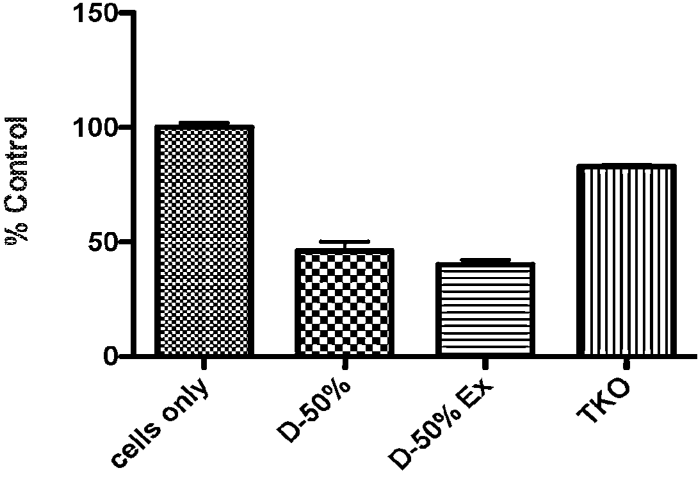
FIG. 14. Graph demonstrating knockdown for organic solvent-free, detergent-free TCVs in HEK cells. siRNA were delivered via organic solvent-free, detergent-free TCV DODMA levels at 50% ("D-50%"), made by T junction mixing), 50% ("D-50% Ex", made by extrusion) and via the commercially available Mirus TKO system (Mirus Bio). The current 50% DODMA formulations showed about 50% knockdown, however, the Mirus TKO system performed worse.

FIG. 14 provides a graph demonstrating knockdown for organic solvent-free, detergent-free TCVs in HEK cells. siRNA were delivered via organic solvent-free, detergent-free TCV DODMA levels at 50% ("D-50%", made by T junction mixing), 50% ("D-50% Ex", made by extrusion), and via the commercially available Mirus TKO system (Mirus Bio). The current 50% DODMA formulations showed about 50% knockdown, while the Mirus TKO system performed significantly worse.

Turning to some further discussion of these Figures, FIG. 12 demonstrates that the bench-top loading of siRNA into empty organic solvent-free, detergent-free TCVs as discussed herein have low-toxicity properties and efficient expression knockdown in primary neuronal cells derived from mice and HEK cell line. For treatment of primary cortical neurons, TCVs were mixed with siRNA at a ratio of about 0.022-0.058 mg nucleic acid: 1 μmole lipid and transferred into wells containing primary neuronal cells. The light micrographs in FIG. 13, all taken at the same magnification, show that in the control and TCV-treated wells, the cells remain healthy with processes intact and very low numbers of dead cells. In the Mirus TransIT-TKO-treated well, the cells appear considerably less healthy, with broken cellular processes and an increased amount of small, condensed (dead) cells.

For FIG. 12, HEK cells were treated with Lipofectamine RNAiMAX and TCVs containing RNP selected cargo. HEK cells were treated with a final concentration of 5-50 nM RNP and either TCV or RNAiMAX reagent. Cell viability was assessed using Promega ONE-Glo+Tox kit, and compared with untreated control cells. HEK cultures treated with RNAiMAX show a significant decrease in overall health compared to both control and TCV-treated wells.

FIG. 14 demonstrates the effectiveness of bench-top loading of empty organic solvent-free, detergent-free TCVs as discussed herein in delivering siRNA selected cargo compared to the commercially-available product, Mirus LT-TKO. The TCVs were incubated with siRNA targeting the luciferase gene for 5-10 minutes at room temperature at a ratio of about 0.022-0.058 mg nucleic acid: 1 μmole lipid. HEK cells were treated with Mirus LT-TKO according to manufacturer's instructions. At the time of treatment, media in the wells was completely replaced with fresh growth media containing either siRNA:TCV or siRNA:Mirus LT-TKO mixtures. After 72 hours of treatment, HEK cells were assayed for cell viability and luciferase output using the Promega ONE-Glo+Tox kit, and all cells were compared to untreated control wells.

REFERENCES

Akinc, A., A. Zumbuehl, et al. (2008). "A combinatorial library of lipid-like materials for delivery of RNAi therapeutics." *Nat Biotechnol* 26(5): 561-569.

Basha, G., M. Ordobadi, et al. (2016). "Lipid Nanoparticle Delivery of siRNA to Osteocytes Leads to Effective Silencing of SOST and Inhibition of Sclerostin In Vivo." *Mol Ther Nucleic Acids* 5(9): e363.

Belliveau, N. M., J. Huft, et al. (2012). "Microfluidic Synthesis of Highly Potent Limit-size Lipid Nanoparticles for In Vivo Delivery of siRNA." *Mol Ther Nucleic Acids* 1: e37.

Chen, S., Y. Y. Tam, et al. (2014). "Development of lipid nanoparticle formulations of siRNA for hepatocyte gene silencing following subcutaneous administration." *J Control Release* 196:106-112.

Chen, S., Y. Y. Tam, et al. (2016). "Influence of particle Size on the in vivo potency of lipid nanoparticle formulations of siRNA." *J Control Release.*

De Souza, R. A., S. A. Islam, et al. (2016). "DNA methylation profiling in human Huntington's disease brain." *Hum Mol Genet* 25(10): 2013-2030.

Digiacomo, L., S. Palchetti, et al. (2018). "Cationic lipid/DNA complexes manufactured by microfluidics and bulk self-assembly exhibit different transfection behavior." *Biochem Biophys Res Commun* 503(2): 508-512.

Hafez, I. M., N. Maurer, et al. (2001). "On the mechanism whereby cationic lipids promote intracellular delivery of polynucleic acids." *Gene Ther* 8(15): 1188-1196.

Jayaraman, M., S. M. Ansell, et al. (2012). "Maximizing the potency of siRNA lipid nanoparticles for hepatic gene silencing in vivo." *Angew Chem Int Ed Engl* 51(34): 8529-8533.

Jeffs, L. B., L. R. Palmer, et al. (2005). "A Scalable, Extrusion-Free Method for Efficient Liposomal Encapsulation of Plasmid DNA." *Pharm Res* 22(3): 362-372.

Kulkarni, J. A., M. M. Darjuan, et al. (2018). "On the Formation and Morphology of Lipid Nanoparticles Containing Ionizable Cationic Lipids and siRNA." *ACS Nano* 12(5): 4787-4795.

Kulkarni, J. A., Y. Y. C. Tam, et al. (2017). "Rapid Synthesis of Lipid Nanoparticles Containing Hydrophobic Inorganic Nanoparticles." *Nanoscale.*

Leung, A. K., I. M. Hafez, et al. (2012). "Lipid Nanoparticles Containing siRNA Synthesized by Microfluidic Mixing Exhibit an Electron-Dense Nanostructured Core." *J Phys Chem C Nanomater Interfaces* 116(34): 18440-18450.

Leung, A. K., Y. Y. Tam, et al. (2015). "Microfluidic Mixing: A General Method for Encapsulating Macromolecules in Lipid Nanoparticle Systems." *J Phys Chem B* 119(28): 8698-8706.

Lin, P. J., Y. Y. Tam, et al. (2013). "Influence of cationic lipid composition on uptake and intracellular processing of lipid nanoparticle formulations of siRNA." *Nanomedicine* 9(2): 233-246.

Maier, M. A., M. Jayaraman, et al. (2013). "Biodegradable lipids enabling rapidly eliminated lipid nanoparticles for systemic delivery of RNAi therapeutics." *Mol Ther* 21(8): 1570-1578.

Maurer, N., K. F. Wong, et al. (2001). "Spontaneous entrapment of polynucleotides upon electrostatic interaction with ethanol-destabilized cationic liposomes." *Biophys J* 80(5): 2310-2326.

Palchetti, S., D. Pozzi, et al. (2017). "Manipulation of lipoplex concentration at the cell surface boosts transfection efficiency in hard-to-transfect cells." *Nanomedicine* 13(2): 681-691.

Pardi, N., S. Tuyishime, et al. (2015). "Expression kinetics of nucleoside-modified mRNA delivered in lipid nanoparticles to mice by various routes." *J Control Release* 217: 345-351.

Pozzi, D., C. Marchini, et al. (2012). "Transfection efficiency boost of cholesterol-containing lipoplexes." *Biochim Biophys Acta* 9(43): 22.

Rungta, R. L., H. B. Choi, et al. (2013). "Lipid Nanoparticle Delivery of siRNA to Silence Neuronal Gene Expression in the Brain." *Mol Ther Nucleic Acids* 3(2): 65.

Sabnis, S., E. S. Kumarasinghe, et al. (2018). "A Novel Amino Lipid Series for mRNA Delivery: Improved Endosomal Escape and Sustained Pharmacology and Safety in Non-human Primates." *Mol Ther* 26(6): 1509-1519.

Scherphof, G. and H. Morselt (1984). "On the size-dependent disintegration of small unilamellar phosphatidylcholine vesicles in rat plasma. Evidence of complete loss of vesicle structure." *Biochem J* 221(2): 423-429.

Semple, S. C., A. Akinc, et al. (2010). "Rational design of cationic lipids for siRNA delivery." *Nat Biotechnol* 28(2): 172-176.

Semple, S. C., S. K. Klimuk, et al. (2001). "Efficient encapsulation of antisense oligonucleotides in lipid vesicles using ionizable aminolipids: formation of novel small multilamellar vesicle structures." *Biochimica et Biophysica Acta (BBA)—Biomembranes* 1510(1): 152-166.

Suhr, O. B., T. Coelho, et al. (2015). "Efficacy and safety of patisiran for familial amyloidotic polyneuropathy: a phase II multi-dose study." *Orphanet Journal of Rare Diseases* 10(1): 109

Tam, P., M. Monck, et al. (2000). "Stabilized plasmid-lipid particles for systemic gene therapy." *Gene Therapy* 7:1867.

Wang, Y., L. Miao, et al. (2015). "Delivery of oligonucleotides with lipid nanoparticles." *Adv Drug Deliv Rev* 87:68-80.

Wheeler, J. J., L. Palmer, et al. (1999). "Stabilized plasmid-lipid particles: construction and characterization." *Gene Ther* 6(2): 271-281.

Zhigaltsev, I. V., N. Belliveau, et al. (2012). "Bottom-up design and synthesis of limit size lipid nanoparticle systems with aqueous and triglyceride cores using millisecond microfluidic mixing." *Langmuir* 28(7): 3633-3640.

Zhigaltsev, I. V., Y. K. Tam, et al. (2016). "Production of limit size nanoliposomal systems with potential utility as ultra-small drug delivery agents." *J Liposome Res* 26(2): 96-102.

All terms used herein are used in accordance with their ordinary meanings unless the context or definition clearly indicates otherwise. Also unless expressly indicated otherwise, in the specification the use of "or" includes "and" and vice-versa. Non-limiting terms are not to be construed as limiting unless expressly stated, or the context clearly indicates, otherwise (for example, "including," "having," and "comprising" typically indicate "including without limitation"). Singular forms, including in the claims, such as "a," "an," and "the" include the plural reference unless expressly stated, or the context clearly indicates, otherwise.

Unless otherwise stated, adjectives herein such as "substantially" and "about" that modify a condition or relationship characteristic of a feature or features of an embodiment, indicate that the condition or characteristic is defined to within tolerances that are acceptable for operation of the embodiment for an application for which it is intended.

The scope of the present devices, systems and methods, etc., includes both means plus function and step plus function concepts. However, the claims are not to be interpreted as indicating a "means plus function" relationship unless the word "means" is specifically recited in a claim, and are to be interpreted as indicating a "means plus function" relationship where the word "means" is specifically recited in a claim. Similarly, the claims are not to be interpreted as indicating a "step plus function" relationship unless the word "step" is specifically recited in a claim, and are to be interpreted as indicating a "step plus function" relationship where the word "step" is specifically recited in a claim.

From the foregoing, it will be appreciated that, although specific embodiments have been discussed herein for purposes of illustration, various modifications may be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion and figures herein.

What is claimed is:

1. A method of transfection, the method comprising administering to a patient a composition comprising a water-based solution which comprises:

(A) a transfection competent vesicle (TCV) comprising lipid components forming the TCV; and (B) a cargo entrapped in the TCV, wherein:

(a) the lipid components consist of: (i) 1,2-Dioleyloxy-3-dimethylamino-propane (DODMA) at 20-30 mol %; (ii) 1,2-dioleoyl-sn-glycero-3-phosphoethanolamine (DOPE) at 20-30 mol %; (iii) 1,2-distearoyl-sn-glycero-3-phosphocholine (DSPC) at 10 mol %; and (iv) cholesterol at 40 mol %; and (b) the cargo comprises a Cas protein and a guide RNA, optionally wherein the patient comprises a human.

2. The method according to claim 1, wherein the administering comprises delivering the composition to the brain of the patient.

3. The method according to claim 1, wherein:

(i) the Cas protein comprises Cas9, Cas10, Cas11, Cas12, or Cpf1; and/or (ii) the cargo further comprises an additional nucleic acid, optionally a single-stranded DNA.

4. A method of transfection, the method comprising transfecting a target cell with a composition comprising a water-based solution which comprises:

(A) a transfection competent vesicle (TCV) comprising lipid components forming the TCV; and (B) a cargo entrapped in the TCV, wherein:

(a) the lipid components consist of: (i) 1,2-Dioleyloxy-3-dimethylamino-propane (DODMA) at 20-30 mol %; (ii) 1,2-dioleoyl-sn-glycero-3-phosphoethanolamine (DOPE) at 20-30 mol %;

(iii) 1,2-distearoyl-sn-glycero-3-phosphocholine (DSPC) at 10 mol %; and (iv) cholesterol at 40 mol %; and (b) the cargo comprises a Cas protein and a guide RNA, wherein the target cell is a mammalian cell, optionally a human cell.

5. The method according to claim 4, wherein:

(i) the Cas protein comprises Cas9, Cas10, Cas11, Cas12, or Cpf1; and/or (ii) the cargo further comprises an additional nucleic acid, optionally a single-stranded DNA.

6. A method for treating Huntington's disease in a patient, the method comprising administering to the brain of the patient a therapeutically effective amount of a composition comprising a water-based solution which comprises:

(A) a transfection competent vesicle (TCV) comprising lipid components forming the TCV; and (B) a cargo entrapped in the TCV, wherein:

(a) the lipid components consist of: (i) 1,2-Dioleyloxy-3-dimethylamino-propane (DODMA) at 20-30 mol %; (ii) 1,2-dioleoyl-sn-glycero-3-phosphoethanolamine (DOPE) at 20-30 mol %; (iii) 1,2-distearoyl-sn-glycero-3-phosphocholine (DSPC) at 10 mol %; and (iv) cholesterol at 40 mol %; and (b) the cargo comprises a ribonucleoprotein (RNP) targeting the huntingtin gene, wherein the RNP comprises a Cas9 protein and a guide RNA, optionally wherein the patient comprises a human.

7. The method according to claim 6, wherein the cargo further comprises an additional nucleic acid, optionally a single-stranded DNA.

* * * * *